United States Patent

Bajard

[11] Patent Number: 6,107,082
[45] Date of Patent: Aug. 22, 2000

[54] PROCESS FOR BACTERIA IDENTIFICATION AND FOR DETERMINATION OF THE SENSITIVITY OF BACTERIA TO ANTIBIOTICS AND APPARATUS AND MEASURING SUPPORTS FOR CARRYING OUT THIS PROCESS

[75] Inventor: Jean Bajard, Griesheim sur Souffel, France

[73] Assignee: Pasteur Sanofi Diagnoistics, Marnes la Coquette, France

[21] Appl. No.: 09/177,611

[22] Filed: Oct. 23, 1998

Related U.S. Application Data

[62] Division of application No. 08/647,233, May 9, 1996, Pat. No. 5,863,754.

[30] Foreign Application Priority Data

May 12, 1995 [FR] France .................................. 95 05817
Apr. 29, 1996 [EP] European Pat. Off. .............. 96440034

[51] Int. Cl.$^7$ .................................................. C12M 1/34
[52] U.S. Cl. .................................. 435/287.3; 435/288.5; 435/288.7; 435/309.1
[58] Field of Search ............................... 435/32, 33, 30, 435/34, 39, 40, 287.3, 288.5, 288.7, 309.1; 422/72, 63–65

[56] References Cited

U.S. PATENT DOCUMENTS

| | | |
|---|---|---|
| 3,772,154 | 11/1973 | Isenberg et al. . |
| 3,832,532 | 8/1974 | Praglin et al. . |
| 4,116,775 | 9/1978 | Charles et al. . |
| 4,154,793 | 5/1979 | Guigan . |
| 4,208,484 | 6/1980 | Sogi et al. . |
| 4,680,164 | 7/1987 | Kelln . |
| 4,812,411 | 3/1989 | Guigan . |
| 5,071,625 | 12/1991 | Kelln et al. . |
| 5,314,825 | 5/1994 | Weyrauch et al. . |

FOREIGN PATENT DOCUMENTS

| | | |
|---|---|---|
| 28463 | 5/1981 | European Pat. Off. . |
| 0 211 334 | 2/1987 | European Pat. Off. . |
| 2280895 | 2/1976 | France . |
| 3-49676 | 3/1991 | Japan . |

Primary Examiner—William H. Beisner
Attorney, Agent, or Firm—Young & Thompson

[57] ABSTRACT

A process for bacteria identification and for determining the sensitivity of bacteria to antibiotics, and a apparatus and measuring supports for carrying out this process. There is manually introduced, by means of a sampling and transfer tool, a given volume of bacterial colony into a primary receiver. This is automatically dispersed within a liquid to form a precalibrated inoculum in the primary receiver. There is automatically carried out total or partial transfer of this precalibrated inoculum between the primary receiver and one or more measuring supports, these transfers being carried out without the precalibrated inoculum being placed in contact with an element other than a sampling and transfer tool and/or the primary receiver and its final measuring support or supports and in such a way that the transferred quantities of bacteria correspond to the quantities required for the analyses to be carried out. The precalibrated inoculum is automatically distributed, optionally after having appropriately diluted it to end up with a definitive calibration in one or more compartments of the measuring supports containing mainly appropriate reagents. Measurements are taken on the content of the compartments during or at the end of one or more incubations undergone by the inoculum in the measuring supports, the measurements taken being registered by a computer and being processed in order to characterized the growth of the bacteria present in the inoculum, to identify them and/or to determine their sensitivity to various antibiotics.

26 Claims, 13 Drawing Sheets

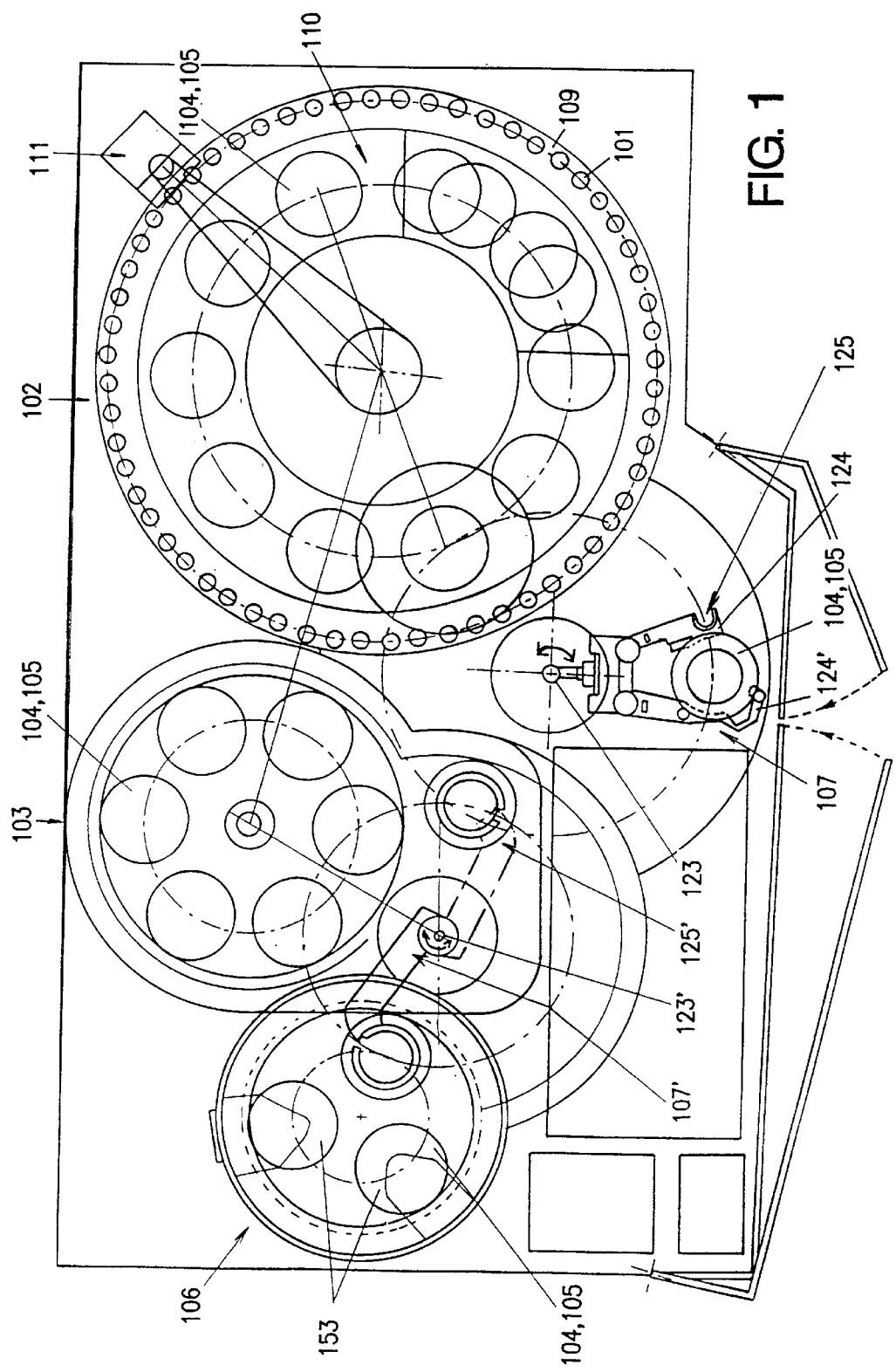

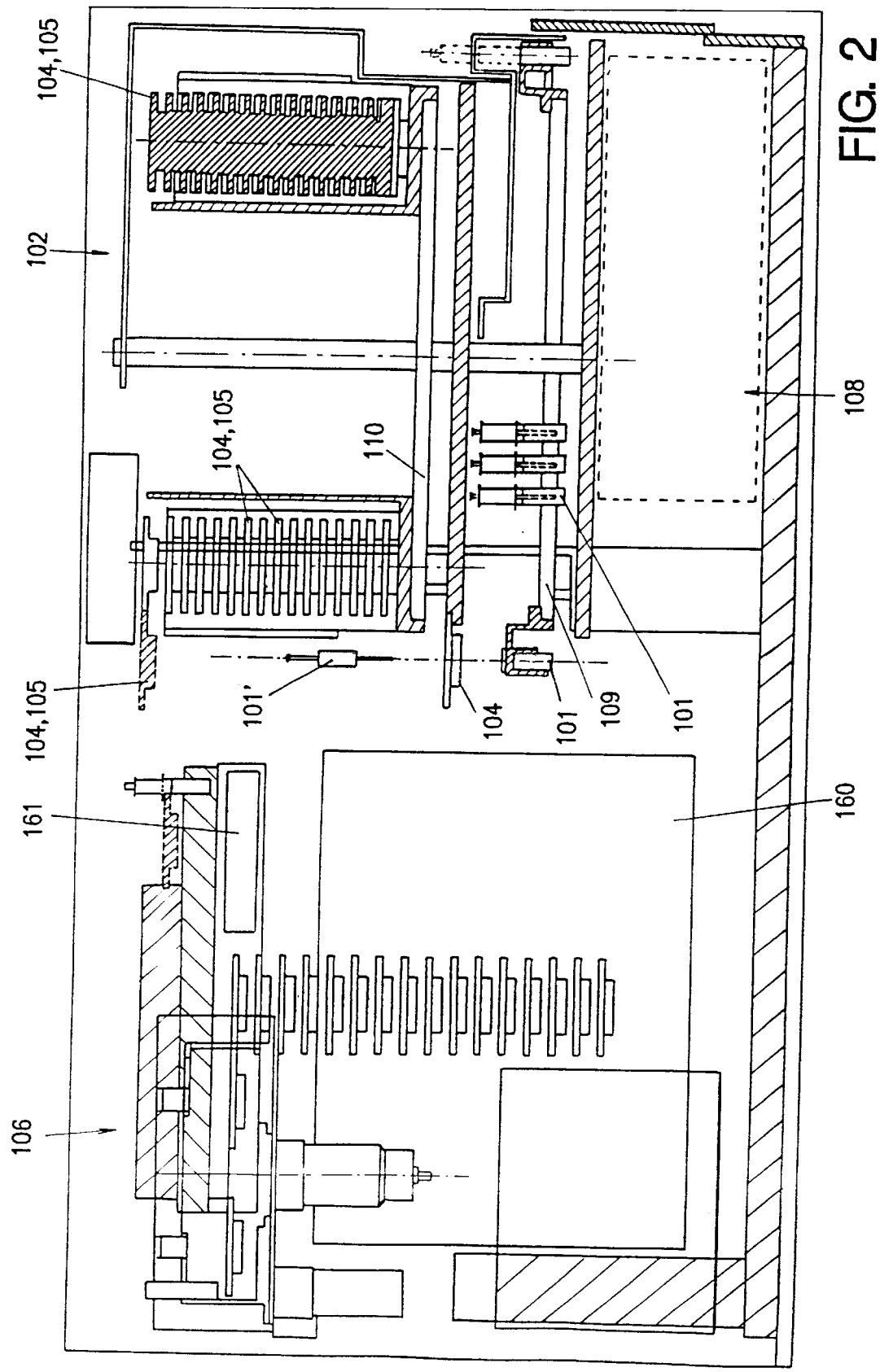

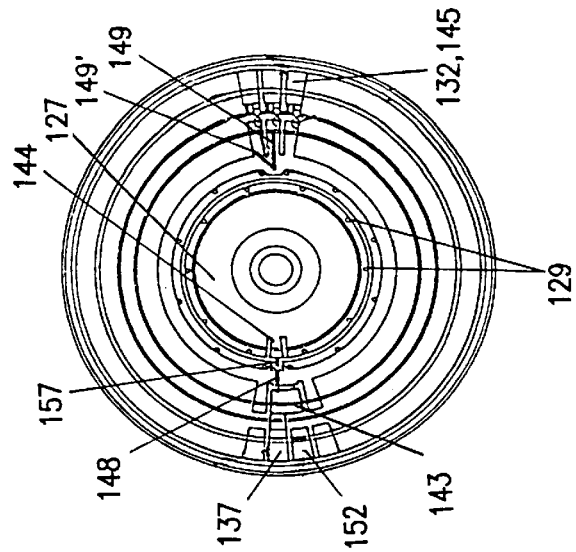
FIG. 6
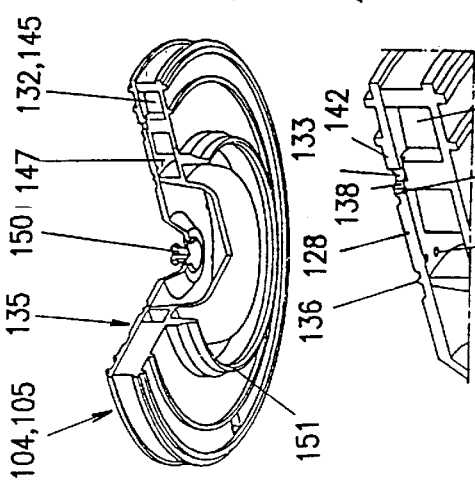
FIG. 4
FIG. 5
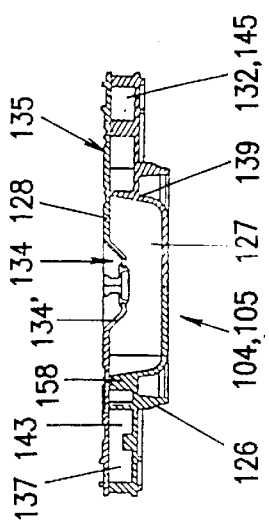
FIG. 3
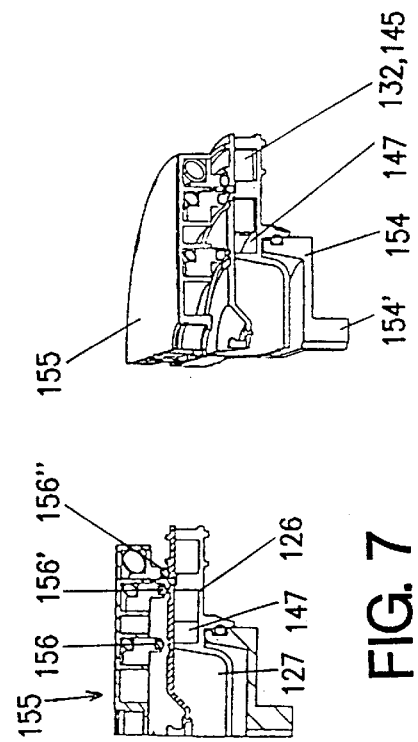
FIG. 8
FIG. 7

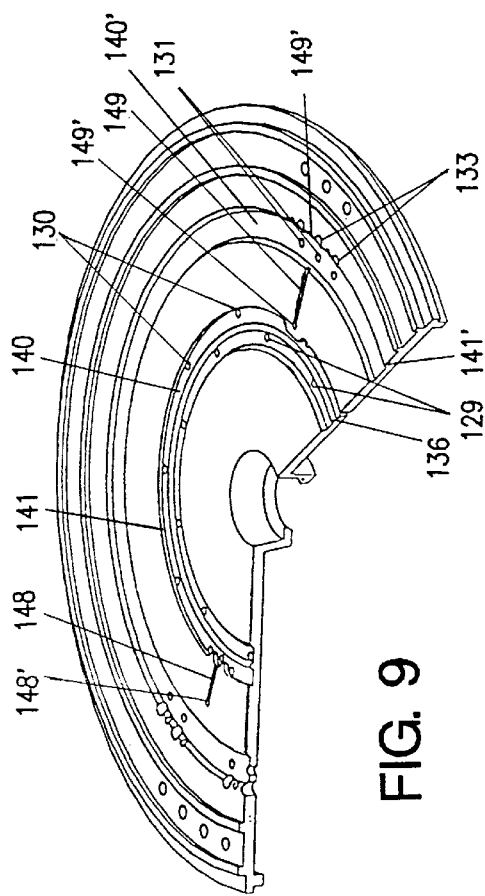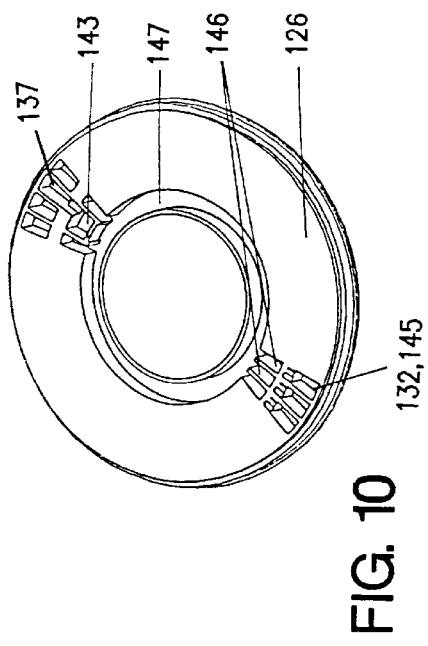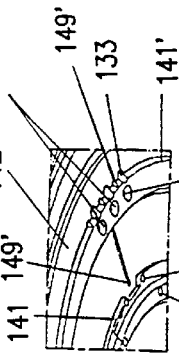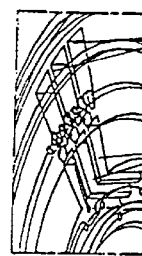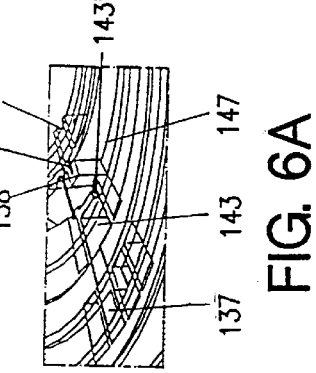

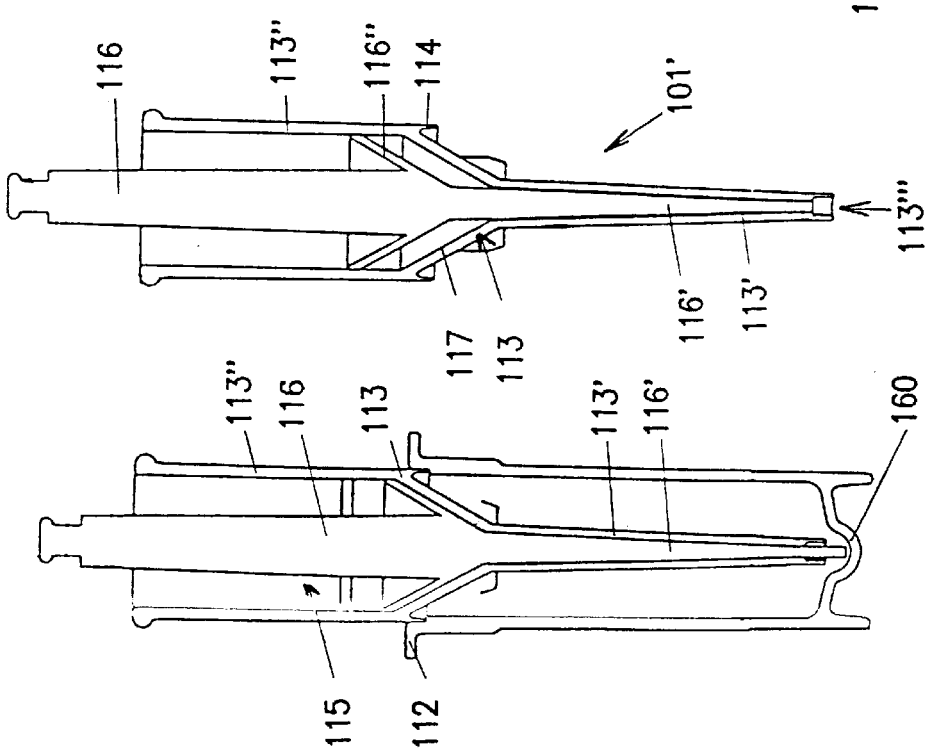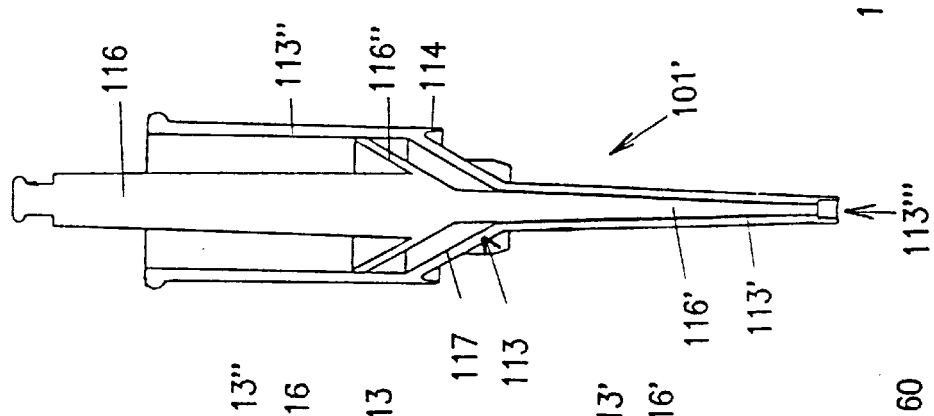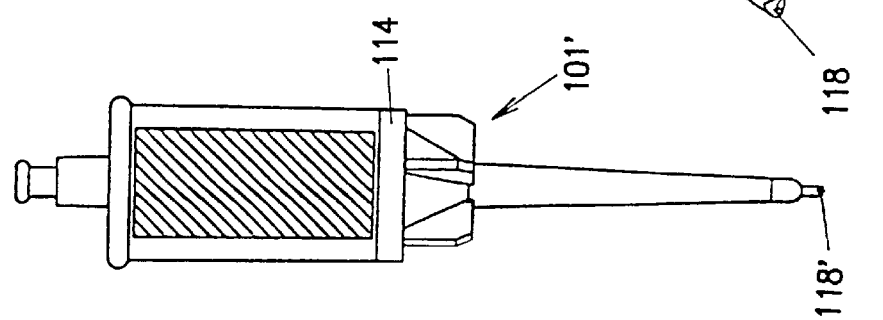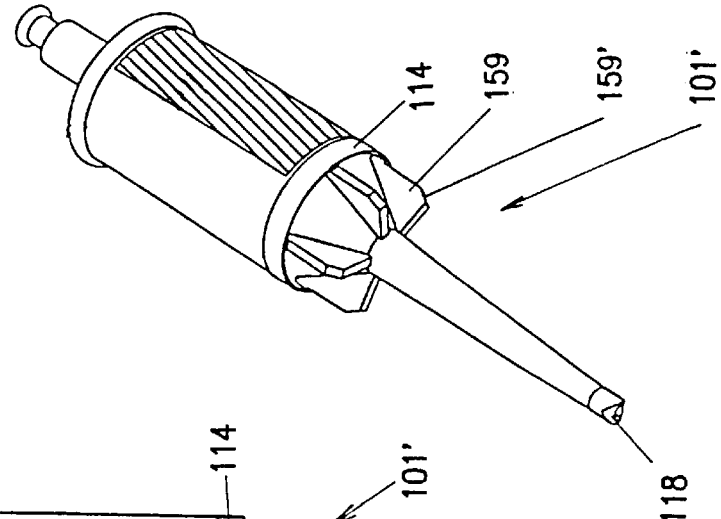

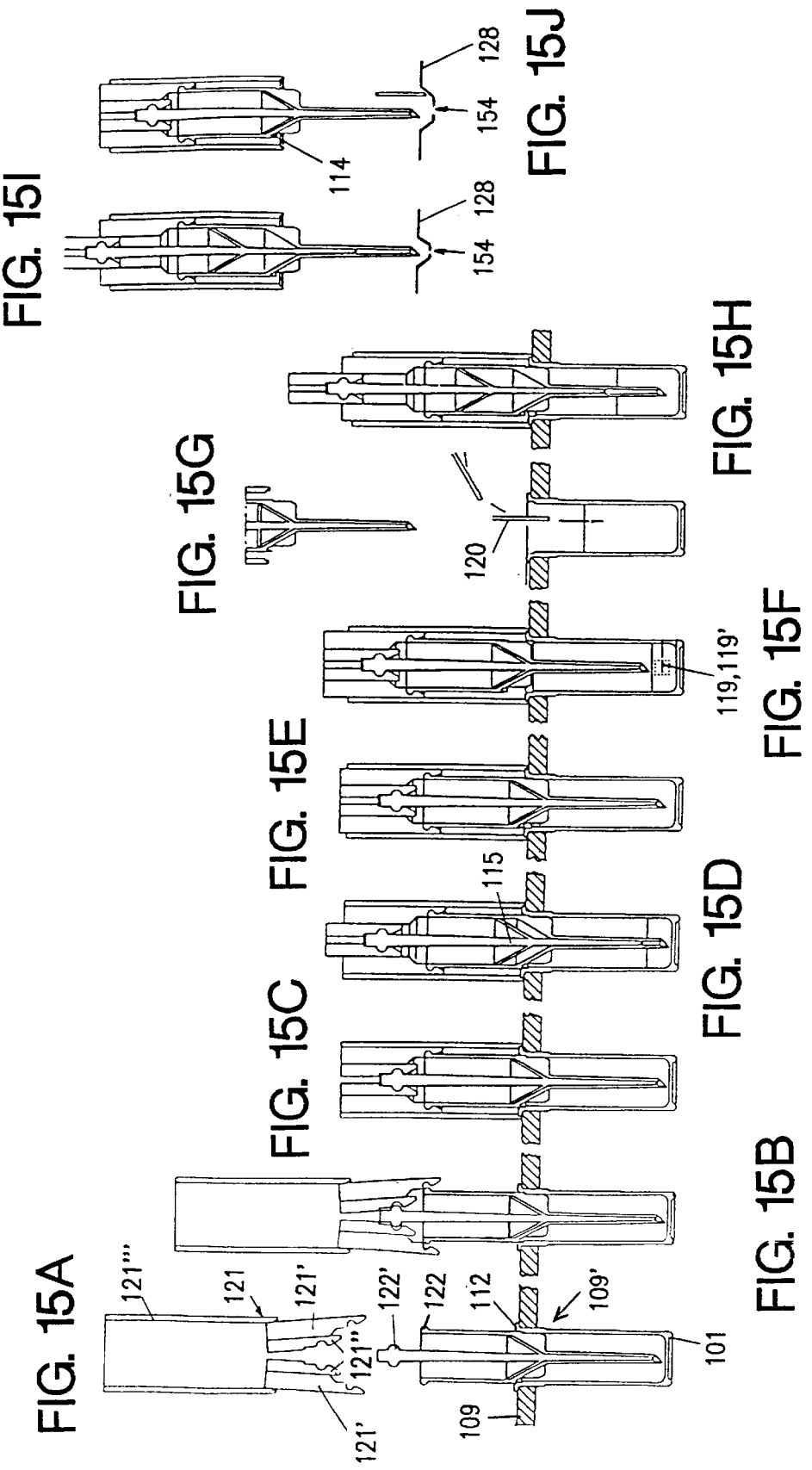

PROCESS FOR BACTERIA IDENTIFICATION AND FOR DETERMINATION OF THE SENSITIVITY OF BACTERIA TO ANTIBIOTICS AND APPARATUS AND MEASURING SUPPORTS FOR CARRYING OUT THIS PROCESS

CROSS-REFERENCE TO RELATED APPLICATIONS

This application is a divisional of application Ser. No. 08/647,233, now U.S. Pat. No. 5,863,754, filed May 9, 1996.

FIELD OF THE INVENTION

The present invention concerns the sphere of microbiology and more particularly bacteriological analysis, in particular the automatic identification of bacteria and the automatic determination of the resistance of bacteria to various antibiotics or automatic antibiogram and relates to a process for bacteria identification and for determination of the sensitivity of bacteria to antibiotics.

BACKGROUND OF THE INVENTION

Starting with a colony, in particular of an inoculum or bacterial suspension, the object of the invention is, on the one hand, to identify bacteria from a set of features measured by photometry and, on the other hand, to carry out growth tests in the presence of an optimum number of antibiotics to demonstrate by nephelometry their action on said bacteria in order to obtain an antibiogram.

To this end, it is worth taking a maximum of measurements with various antibiotics during the same test.

The inoculum is a suspension of bacteria associated with a sample and a patient. It is prepared manually by transfer into an aqueous solution of one or more colonies cultivated in a culture medium in the form of a gel or of elements prepared from urine or from a haemoculture. In fact, after detecting the presence of bacteria, for example by monitoring the variation in the $CO_2$ above a culture of the sample to be analyzed, the sample to be analyzed is transplanted into a second culture in gel form, this transplantation causing the isolation of a specific type of bacteria to the detriment of others and allowing the obtaining of a monobacterial strain. This strain is then used to produce the inoculum by suspension in an aqueous solution.

Generally speaking, bacteria in suspension in inoculums have relatively reduced virulence owing to the preparation treatment, leading to difficulties in rapid experimentation, the various culturing processes with reagents developing relatively slowly.

Various processes and devices for producing an antibiogram are currently known which use, as a support where the measurements are taken, either individual transparent receivers for receiving bacterial culture (FR-A-2 091 133) or multiple transparent receivers arranged in the form of compartments an plane plates (FR-A-2 449 891, EP-A-0 253 685, DE-A-25 21 025 and US-A-3 942 899).

These processes and devices generally involve displacing the measuring support or supports in front of a source of luminous radiation and measuring the luminous intensity of the beam in one or more directions after it has passed through the receiver or receivers and their content.

The receiver or receivers are supplied with bacterial solution in a known manner, either using manual pipettes or using an automatic pipetting device according to EP-A-0 522 602, the various antibiotics being positioned manually in the various receivers before the filling thereof.

Furthermore, FR-A-2 354 554 describes a tubular compartmental receiver allowing the automatic dispersion of a bacterial culture in various peripheral compartments. These peripheral compartments can each be provided, prior to their supply with bacterial culture, with antibiotics arranged in their bottom in the form of dehydrated reagent.

FR-A-2 280 895 also discloses a fractionation device adapted for use in nephelometry or in photometry and having the form of a disc provided on its periphery with compartments for receiving a reagent in solid form and a bacterial solution, the bacterial solution being transferred from a central chamber to the various compartments by centrifugation.

These various known processes and devices allow photometric and nephelometric measurements to be taken by a series of distinct measurements using distinct containers.

However, these known devices and processes do not allow these measurements to be taken rapidly and successively without manual intervention or with an automatic supply of the measuring supports from a same container while also allowing the implementation of simultaneous operations of identification and antibiogram, even from a low-concentration initial inoculum.

SUMMARY OF THE INVENTION

The object of the invention is to overcome these drawbacks by proposing a process and a means allowing automatic identification and determination without manual intervention on the media.

To this end, it relates to a process for bacteria identification and determination of the sensitivity of bacteria to antibiotics in antibiogram formed, characterized in that it involves manually introducing, by means of a sampling and transfer tool, a given volume of bacterial colony into a primary receiver, automatically dispersing this bacterial colony within a liquid to form an at least precalibrated inoculum in said primary receiver, also automatically carrying out total or partial transfer of this precalibrated inoculum between said primary receiver and one or more measuring supports intended to carry out respectively the identification, the antibiogram or these two determinations simultaneously in a single combined operation, said transfers being carried out without the precalibrated inoculum being placed in contact with an element other than, on the one hand, a sampling and transfer tool and/or the primary receiver and, on the other hand, its final measuring support or supports and in such a way that the transferred quantities of bacteria correspond to the quantities required for the analyses to be carried out, automatically distributing the precalibrated inoculum, optionally after having appropriately diluted it to end up with a definitive calibration in one or more compartments of said measuring supports mainly containing appropriate reagents, carrying out in certain cases, in particular for the antibiogram, within a measuring support a so-called pre-growth operation intended to enable the bacteria to multiply rapidly before being subjected to analysis and taking measurements on the content of said compartments during or at the end of one or more incubations undergone by the inoculum in said measuring supports, the measurements taken being registered by a computer and being processed in order to characterize the growth of the bacteria present in the inoculum, to identify them and/or to determine their sensitivity to various antibiotics.

The invention also relates to apparatuses and to measuring supports, in the form of consumables, for carrying out this process and variations thereof which will be described in detail with reference to the drawings enumerated hereinafter.

BRIEF DESCRIPTION OF THE INVENTION

The invention will be understood better by means of the following description which relates to preferred embodiments given as nonlimiting examples and explained with reference to the accompanying schematic drawings.

FIG. 1 is a plan view of the interior of an apparatus for carrying out the process according to the invention according to a first embodiment.

FIG. 2 is a lateral elevation and section of the apparatus according to FIG. 1.

FIG. 3 is a lateral elevation and section of a measuring support according to the invention.

FIG. 4 is a perspective view, partially in section, of a measuring support shown in FIG. 3.

FIG. 5 shows a detail, on a different scale, of a part of the measuring support shown in FIG. 4.

FIG. 6 is a simplified plan view in transparency of a measuring support according to the invention.

FIGS. 6A and 6B show details, in perspective, on a different scale, of two distinct parts of the measuring support shown in FIG. 6.

FIG. 7 is a half view in cross section and in a lateral elevation of a measuring support mounted in a measuring and centrifugation station.

FIG. 8 is a partial section and perspective view of a measuring support mounted in a measuring and centrifugation station.

FIG. 9 is a perspective view, partially in section, of a cover forming the upper wall of a measuring support shown in FIG. 3.

FIG. 9A shows a detail, in a different perspective, of a part of the cover shown in FIG. 9.

FIG. 10 is a simplified view in perspective of a main body forming part of the measuring support shown in FIG. 3.

FIG. 11 shows a lateral elevation in section of a unit comprising primary receiver and sampling and transfer tool.

FIG. 12 is a section of a sampling and transfer tool.

FIGS. 13 and 14 are a lateral elevation and perspective view of a sampling and transfer tool.

FIGS. 15A to 15J show various successive phases of handling for preparing a precalibrated inoculum in the primary receiver and its at least partial transfer into a measuring support.

DETAILED DESCRIPTION OF THE INVENTION

Figure 16:
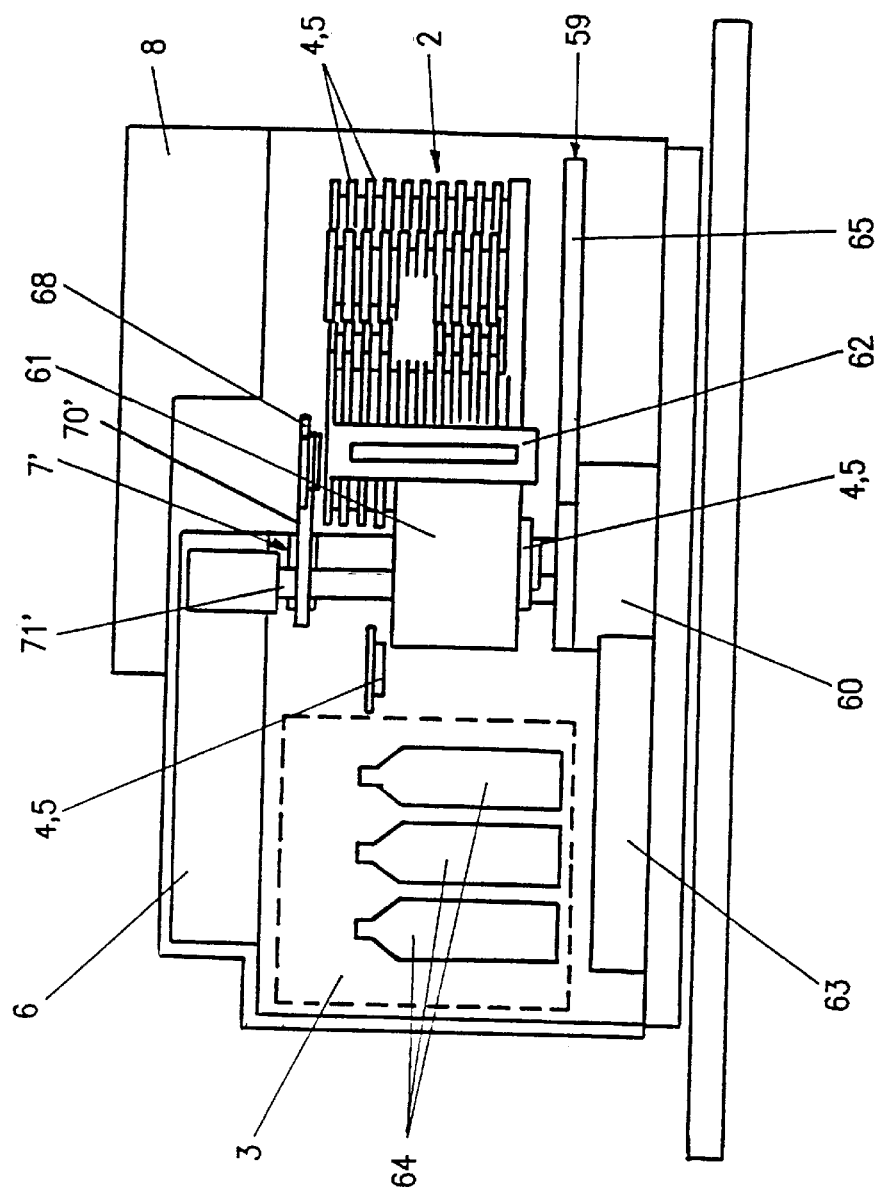
FIG. 16 is an elevation and section of an apparatus for carrying out a variation of the process according to the invention.

According to the invention, the process for bacteria identification and determination of the sensitivity of bacteria to antibiotics in antibiogram form involves manually introducing, by means of a sampling and transfer tool 101', a given volume of bacterial colony into a primary receiver 1; 101, automatically dispersing this bacterial colony within a liquid to form an at least precalibrated inoculum in said primary receiver 1; 101, also automatically carrying out total or partial transfer of this precalibrated inoculum between said primary receiver 1; 101 and one or more measuring supports 4, 5; 104, 105 intended to carry out respectively the identification, the antibiogram or these two determinations simultaneously in a single combined operation, said transfers being carried out without the precalibrated inoculum being placed in contact with an element other than, on the one hand, a sampling and transfer tool 101'; 1, 101 and/or the primary receiver 1; 101 and, on the other hand, its final measuring support or supports 4, 5; 104, 105 and in such a way that the transferred quantities of bacteria correspond to the quantities required for the analyses to be carried out, automatically distributing the precalibrated inoculum, optionally after having appropriately diluted it to end up with a definitive calibration in one or more compartments 32, 37, 45; 132, 137, 145 of said measuring supports 4, 5; 104, 105 mainly containing appropriate reagents, carrying out in certain cases, in particular for the antibiogram, within a measuring support 4; 104 a so-called pre-growth operation intended to enable the bacteria to multiply rapidly before being subjected to analysis and taking measurements on the content of said compartments 32, 37, 45; 132, 137, 145 during or at the end of one or more incubations undergone by the inoculum in said measuring supports 4, 5; 104, 105, the measurements taken being registered by a computer 8; 108 and being processed in order to characterize the growth of the bacteria present in the inoculum, to identify them and/or to determine their sensitivity to various antibiotics.

According to a first embodiment of the invention, the sampling of a given volume of bacterial colony and the transfers of the volumes of precalibrated inoculum into the measuring supports 104, 105 are carried out by means of a single sampling and transfer tool 101' cooperating, for example by sealed fitting, with the primary receiver 101, the volumes of precalibrated inoculum to be transferred being determined by optical measurement of the bacterial concentration of said inoculum carried out in the primary receiver 101 and calculated as a function of the quantities of bacteria required.

The sampling and introduction into the primary receiver 101 of a given volume of bacterial colony are carried out by means of a sampling and transfer tool 101' after the shaping thereof in order to sample the desired volume, (selection of a volume from two different volumes available) and the transfers of precalibrated inoculum from the primary receiver 101 to the measuring supports 104, 105 are carried out by pipetting predetermined volumes of inoculum.

The transfer of the inoculum within the measuring supports 104, 105, in particular to the compartments 132, 145, is monitored dynamically or actively by controlling the opening or the sealed blockage of successive passages leading progressively to said compartments 132, 145.

When using measuring supports for determining antibiograms or carrying out combined determination of antibiogram and identification, the pre-growth of the calibrated inoculum is carried out by a first incubation known as pre-incubation during which the bacteria present in the inoculum are incubated without being placed in the presence of reagents until a beginning of bacterial growth is measurable or until the bacterial concentration reaches a predefined level, this pre-growth being followed by putting the inoculum in contact with the reagents and final incubation during which their interactions are observed.

According to an advantageous practical embodiment of the invention, the distribution of the inoculum in the compartments 32, 37, 45; 132, 137, 145 situated at the periphery of the measuring supports 4, 5; 104, 105 is carried out by centrifugation, the measurements and observations made in the region of said compartments 32, 37, 45; 132, 137, 145 being carried out by rotating the measuring supports 4, 5; 104, 105 round the central axis of centrifugation of said supports.

According to the invention, it is proposed moreover that the measurement of the concentration of bacterial inoculum and the determination of the beginning of growth are effected by photometric measurement carried out on an aliquot part of the inoculum transferred for this purpose, by a first centrifugation in a specific peripheral compartment 37; 137 dedicated to the characterization of the growth during pre-incubation and not containing reagents, the remainder of inoculum remaining blocked during pre-incubation in a central concentric chamber 27; 127 of said support 4; 104, before being transferred, after completion of pre-growth, into the other peripheral compartments 32; 132 by a second centrifugation preceded by an appropriate action of authorization or unblocking, opening the passage for the transfer of the remainder of the inoculum to said other compartments 32; 132 containing reagents.

To prevent contamination of the calibrated or non-calibrated inoculum present in the antibiogram measuring support 104, the passage from the pre-incubation stage to the incubation stage is carried out without breaking the confinement of the interior of the rotating measuring support concerned 4; 104 relative to the exterior, said support remaining closed and said passage being carried out by an interruption in an action on a blocking element participating in the production of this confinement.

According to a preferred embodiment of the invention, the photometric measurements are taken by nephelometry in the case of the measuring supports 4; 104 used for the antibiogram and by determination of absorbency or optical density in the case of the measuring supports 5; 105 used for identification or for combined identification/antibiogram determinations. It is also possible to take fluorimetric measurements by addition of a fluorogenic marker to the reagent.

The invention also relates to a disc-shaped measuring support which can advantageously be used, in particular, in the scope of the process described hereinbefore but which can also be applied more generally in other analysis or identification processes using rotating measuring supports and carrying out monitored transfers of substances to be analyzed within said measuring supports.

As shown in FIGS. 3 to 15 of the accompanying drawings, the measuring support 104, 105 comprises a rigid main body 126 limiting, in the form of non-communicating enclosures, a central chamber 127 and several peripheral compartments 132, 145 each having a catching niche 146.

According to the invention, the main body 126 has an upper wall 128 provided with several sets of traversing transfer orifices 129, 130, 131, 133 respectively opening into the cylindrical central chamber 127, in each catching niche 146 allocated to each compartment 132, 145 and in each of said compartments 132, 145 and covered, with the exception of a central portion surrounding the charging orifice 134 of said central chamber 127 and of the zone of the measurement windows of the compartments 132, 145, by a snugly fitting sealed floating membrane 135 fixed locally and hermetically in particular in the vicinity of the external periphery of the measuring support and round the charging orifice 134 of said upper wall 128 and being able to be pressed intimately against the upper surface of said wall 128 to form sealed temporary zones of contact extending between or covering some of said sets of traversing orifices 129, 130, 131, 133, in particular during the rotation of said measuring support.

It will be noted that, owing to this arrangement, the transfer of the substance to be analyzed or identified, such as a bacterial inoculum, initially injected into the central chamber 127 toward the measuring compartments 132, 145 located at the periphery of said support 104, 105 can be carried out progressively and in a perfectly controlled manner as a function of the successive operations to be carried out.

According to a preferred embodiment of the invention, the upper wall 128 comprises, in the region of its upper face, concentric annular grooves or indentations 140, 140' in which there open the traversing orifices 129, 130, 131, 133 arranged in spaced concentric circles, the internal groove 140 comprising a rib 136 forming an annular contact surface and separating the outlet orifices 129 of the central chamber 127 and the inlet orifices 130 of the annular concentric chamber 147 comprising the radial catching niches 146, and the outlet orifices 131 of the catching niches 146 opening in the region of the upper face of a concentric circular rib or of distinct protruding structures 138, for example in the form of domes, arranged in the external groove 140', the upper ends of the rib 136 and of the structures 138 being located in a plane or planes extending slightly back from the plane of adhesion of the snugly fitting sealed membrane 135.

The provision of points or zones for the support of the membrane 135 which protrude relative to the adjacent surface of the bottoms of annular grooves 140, 140' made in the upper face of the upper wall 128 but stopping at least slightly below the plane of adhesion of the snugly fitting membrane 135 and shaped with a restrained upper face and limited relative to said adjacent surface, allows a reproducible increased seal to be obtained, allows the sealed zones of contact to be located precisely and allows increased resistance thereof to the pressure exerted by the substance or the inoculum to be obtained during the rotation of the measuring supports 104, 105, said zones of contact being located at the peaks forming obstacles to the centripetal progression of the substance or of the inoculum.

To facilitate the transfers and the complete emptying of the central chamber 127 and of the catching niches 146, the central chamber 127 can comprise a peripheral lateral wall 139 which is inclined at least slightly outwardly in the direction of the upper wall 128, the outlet orifices 129 of the central chamber 127 and the outlet orifices 131 of the catching and equi-distribution niches 146 being located substantially in the alignment of the internal faces of the peripheral lateral walls 139', 146' thereof.

In order to direct the flow of substance or of inoculum preferentially toward the inlet orifices during the rotation of the measuring supports 104, 105, said inlet orifices 130 of the concentric chamber 147 comprising catching and equi-distribution niches 146 open at the upper face of the upper wall 128 at the foot of an offset 141 limiting, laterally and on the external side, the internal annular indentation 140, and the inlet orifices 133 of the measuring compartments 132, 145 open and the inlet orifices 133 of the compartments at the base or in an inclined flank 141' of a circular offset opening at an external protruding surface 142 being able to form a zone of contact or of external adhesion of the snugly fitting floating membrane 135.

The floating membrane has, for example, a composite structure comprising, for example, an external layer of paper (acting as a printing support), an intermediate layer of aluminium and an internal layer of hot-melting adhesive.

The fixing of the membrane 135 in the region of its zones of connection to the upper wall 128 can thus be carried out by pressing said membrane 135 intimately onto said wall 128 in the region of said zones and by inducing a heating current into the aluminium layer which causes the layer of internal adhesive to melt.

The rib 136 and the projecting or protruding structures 138 have heights which are such that their upper faces are located slightly below the plane of adhesion of the membrane 135 with the result that the membrane 135 will not adhere at their level when the layer of hot-melting adhesive melts.

According to a further characteristic of the invention shown, in particular, in FIGS. 3, 6, 6A and 10 of the accompanying drawings, the measuring support 104, 105 can comprise a pre-incubation compartment 137 identical to the other peripheral compartments 132, 145, aligned circularly therewith and communicating with a closed pre-chamber 143 formed in the concentric chamber 147 enclosing the latching and equi-distribution niches 146 and supplied with inoculum from an internal catching niche 144 located in the region of a portion of the peripheral lateral wall 139 of the central chamber 127, by means of a passage not blockable by the sealed zones of contact 136, 138, 142 capable of being formed between the snugly fitting membrane 135 and the upper wall 128.

It is advantageous if the supply passage of the pre-chamber 143, communicating freely with the pre-incubation compartment 137 and also forming an overflow for the catching niches 146, consists of a conduit 157 beginning in the upper part of the portion of peripheral lateral wall 139 limiting the internal latching niche 144 formed by cooperation between a groove made in the upper part of a radial projecting extension 158 of the peripheral lateral wall 139 of the central chamber 127 and of the upper wall 128 and opening into or at the inlet of a groove 148 with a centripetal radial extension dug in the upper face of the upper wall 128, forming a sealed conduit in cooperation with the membrane 135 stuck on either side of said groove 148 and of which the distal end terminates in the region of a traversing orifice 148' opening in the pre-chamber 143.

The pre-chamber 143 projects into the annular concentric chamber 147 by a distance substantially equal to the length of the portions of wall limiting the catching niches 146 and has, in the region of the upper part of its wall parallel to the peripheral lateral wall 139 of the central chamber 127, a very fine capillary orifice 143' forming a passage for the evacuation of the overflow during the equi-distribution phase.

Although FIGS. 6 and 10 in particular only show a limited number of compartments 132, 145, it is obviously understood that these compartments are arranged over the entire periphery of the measuring supports 104 and 105 and number, for example, about fifty.

According to a preferred embodiment of the measuring support 104, 105, the upper wall 128 can consist of an added cover which is fixed by fitting and adhesion or welding in the region of the external peripheral wall of the main body 126 and comprises additional orifices 149 and radial superficial grooves 149' allowing the return of air during the transfers of the substance to be analyzed which is injected into the central chamber 127 toward the periphery of said support 104, 105.

Such a design of the support 104, 105 allows its three components to be produced independently, that is the main body 126, the cover 128 and the membrane 135, then to be assembled in a suitable manner, the main body and the cover 128 being obtained, for example, by injection moulding of a preferably transparent thermoplastic material.

If two rotating measuring supports 104, 105 of different natures are used, such as rotating supports 104 in the case of antibiogram and rotating supports 105 for identification, these supports can have the same constitution and can be distinguished solely by the nature of the reagents arranged in their respective measuring compartments 132, 145 and by the handling to which they will be subjected in use (presence or absence of a pre-incubation phase).

Such a similarity in the structure of measuring supports 104, 105 intended for different applications substantially facilitates standardization of manufacture, leads to a lower cost price than for differentiated supports, facilitates the handling thereof by the treatment and analysis apparatus and allows the constitution thereof to be simplified.

As shown, in particular, in FIGS. 3 and 4 of the accompanying drawings, the charging orifice 134 of the central chamber 127 is located in an indentation 134' in the upper wall 128 and is blockable by means of a stopper 150 of which the upper part is substantially level with the upper face of the upper wall 128.

Therefore, no part will exceed the plane containing the upper face of the upper wall 128.

The indentation 134' can be limited by walls forming a truncated cone shaped cylindrical structure directed toward the charging orifice 134 (FIGS. 3 and 4).

For the handling and storage by stacking of the measuring supports 104, 105, the bottom of the central chamber 127 is surrounded by a concentric gripping and rigidifying sleeve 151 projecting in the region of the lower face of the support 104, 105. Said supports can also comprise rigidifying and guiding ribs in the region of their peripheral compartments.

Furthermore, to facilitate adjustment and setting of the photometric measuring devices, the measuring supports 104, 105 can each comprise a traversing aperture 152 having dimensions identical to those of a compartment 132, 145 located in circular alignment therewith and which is made in the main body 126 and in the upper wall 128, said aperture 152 preferably being located adjacently to the pre-incubation compartment 137 so as to allow easy marking thereof.

Finally, the upper wall 128 is equipped, above each compartment 132, 137, 145 and close to its external edge, with a measuring window, a similar window being provided in each of the wall portions of the main body 126 respectively constituting the bottoms of said compartments opposite each aforementioned measuring window and at least one indexing reflecting zone formed on the external face of the external peripheral wall of the main body 126 being associated with each compartment 132, 137, 145 with an angular offset which is fixed relative thereto.

The inclined reflective zones create offset optical marks for the various measuring compartments 132, 137, 145 and allow guided centring of the photometric measuring devices in the region of each of said compartments.

Thus, the measuring supports 104, 105 comprise a partitioned closed body (main body 126+upper wall 128) pierced at predetermined locations by small orifices 129, 130, 131, 133 and topped by a snugly fitting flexible sealed membrane 135 allowing, by controlled action on said membrane and in the scope of the process described hereinbefore:

the substance to be analyzed to be kept in the centre of the measuring support under consideration during a homogenization and, if applicable, pre-incubation phase;

the substance to be analyzed to be kept in the zone of the annular concentric chamber 147 and of the radial catching niches 146, while isolating them from the measuring compartments 132, 145 during the equidistribution phase of the substance to be analyzed by centrifugation, wherein centrifugation can be carried out for the period required for obtaining perfect equidistribution of the substance to be analyzed in said niches by means of an overflow function assured by the pre-chamber 143 and the pre-incubation compartment 137 by means of the capillary orifice 143', or;

the passage between the radial latching niches 146 and the measuring compartments 132, 145 to be opened so as to transfer the substance to be analyzed from said niches toward said compartments during a centrifugation operation.

The invention also relates to an apparatus for carrying out the above-described process, shown in FIGS. 1 and 2 of the accompanying drawings, said apparatus essentially consisting of a first fresh module 102 for support and for storage of measuring supports 104, 105 as described hereinbefore and of primary receivers 101 each cooperating with a corresponding sampling and transfer tool 101', of a second module 103 for the incubation of the supports 104 and 105, after injection of the bacterial inoculum, of a third module 106 for centrifugation and nephelometric and/or photometric and/or fluorimetric measurement, of one or more transfer devices 107, 107' serving said modules 102, 103 and 106 and of a computer 108 for monitoring and controlling the various stages of the process and acquiring, registering, processing, evaluating and/or restoring data, the second and third modules 103 and 106 being arranged in a confinement enclosure.

According to the invention, the primary receivers 101 are carried by a crown-shaped supporting means 109 extending concentrically round and beneath a disc-shaped supporting means 110 bearing the measuring supports 104, 105, the two supporting means 109, 110 being mounted with the ability to rotate round the same axis and each primary receiver 101 being bringable, by mere rotation of said crown-shaped supporting means 109, into the region of a station 111 for handling of the associated tool 101' for sampling and transfer and for optical density measurement of the content of said primary receiver 101.

As shown in particular in FIGS. 11 to 14 of the accompanying drawings, each primary receiver 101 for receiving a given volume of bacterial colony and for preparation of an at least precalibrated inoculum has the form of a cylindrical receiver which is open in the region of its upper part equipped with a radial rim 112 for holding said primary receiver 101 in one of the corresponding recesses 109' made in the crown-shaped moving support 109.

The sampling and transfer tool 101' can advantageously consist of a syringe of which the body 113 comprises a frontal tapered part for sampling and ejection 113' and a substantially cylindrical rear part 113" for storage and gripping, said rear part 113" having at least one external radial offset 114 in the region of its end adjacent to the front part 113' for partial fitting with blocking of said body 113 in the primary receiver 101, the frontal free end of the frontal part 113' thus being located at a short distance from the bottom of said primary receiver 101.

The rear part 113" can comprise lower extensions 159 in the form of radial fins extending from the offset 114 and each provided with a lower lateral bevel 159', these extensions assisting the centring of the fitting of the tool 101' in the primary receiver 101 and the locking of its radial position therein.

According to a characteristic of the invention also shown in FIGS. 11 to 14 of the accompany drawings, the syringe 101' comprises, in the region of its front end, means 118, 118' for sampling a reduced quantity or a normal quantity of bacterial colony, by volume, as a function of the positioning of its piston 115.

The piston 115 of the syringe 101' consists of a tapered actuating rod 116 of which the front part 116' cooperates with the front part 113' of the body 113 and can exceed the sampling and ejection aperture 113''' of said front part 113' of the body 113 with its free end when the piston 115 is totally immersed in the body 113, said actuating rod 116 having a radial offset 116" mating with the bottom 117 of the internal volume of the cylindrical rear part 113" of the body 113 when said piston 115 is completely immersed in said body 113.

As shown in FIG. 11 of the accompanying drawings, the bottom of the primary receiver 101 can have a central indentation 160 for receiving the front free end of the actuating rod 116 when it extends beyond the front end of the front part 113' of the body 113.

In order to be able to obtain an at least precalibrated inoculum in the primary receiver 101 by at least rough determination of the quantity of elements of bacterial colony taken (manual sampling or microsampling), depending in particular on the type of analysis envisaged, the free ends of the front parts 113', 116' of the body 113 and of the actuating rod 116 of the piston 115 are provided with an offset or with an indentation 118, 118' forming surfaces or volumes for sampling of different determined quantities of bacterial colony, the free end of the front part 116' of the actuating rod 116 being operational for sampling when the piston 115 is completely immersed and the free end of the front part 113' of the body 113 being operational when the piston 115 is at least slightly retracted in said front part 113".

The precalibrated inoculum is made up by injection of a fixed quantity of dilution liquid, liquid injected by a means 120.

In order to determine the bacteria concentration of the precalibrated inoculum, each primary receiver 101 comprises in its lateral wall, in the vicinity of its bottom, two opposing measuring windows 119, 119' adapted to measure the optical density of the content of said primary receiver 101 at the station 111, the station 111 also comprising the means 120 for injection of dilution liquid into said primary receiver 101.

It should be added that the quantity of inoculum taken from the primary receiver 101 and injected into the target measuring supports 104, 105 can easily be adjusted by calculating the volume to be transferred in view of the bacteria concentration measured by optical density owing to the use of a sampling and transfer tool 101' in the form of a syringe which is handled automatically by a means adapted to the region of the station 111 in particular.

This means 121 for handling of the syringe 101' can consist, for example, as shown in FIGS. 15A to 15J of the accompanying drawings, of two sets of jaws 121' and 121" comprising two external jaws 121' intended to engage in a rigid, blocking manner with a radial rim 128 in the region of the aperture of the rear part 113" of the body 113 and two internal jaws 121" arranged concentrically between the two external jaws 121' intended to engage in a rigid and blocking manner with a swelling 122' of the actuating rod 116, the two sets of jaws 121', 121" being closed separately or preferably simultaneously by sliding a sleeve 121''' round and along the external jaws 121', the internal jaws 121" being able to slide relative to the external jaws 121', in particular in the closure position, and to the sleeve 121''' and the latter being able to rest on the crown-shaped moving support 109 and on the radial edge 112 of the upper aperture of the considered primary receiver 101 so as to block it in position in its recess 109' during the sliding of any one of the two sets of jaws 121', 121".

The preparation of an at least precalibrated inoculum in a primary receiver 101 and its at least partial transfer in a controlled quantity into a measuring support 104, 105 will now be described in more detail with reference to FIGS. 15A and 15J of the accompanying drawings.

Firstly, the operator takes a predetermined volume of bacterial colony manually using the tool 101', this volume being defined by adjustment of said tool 101' by displacing the piston 115 into a position corresponding to total immersion (passing beyond the front end of the front part 116' of the actuating rod 116 in the region of the aperture 113" of the body 113) or to slight retraction of said actuating rod. In the retracted position of the piston 115, the tool 101' collects a quantity of bacteria constituting a so-called normal sample whereas in the immersed position of the piston the tool 101' collects a so-called reduced sample or microsample (about 1/100 of the former).

The tool 101' carrying a predetermined quantity of bacterial colony is then fitted in a primary receiver 101 and the unit thus formed is arranged in a recess 109' in the supporting means 109.

At the beginning of preparation of the inoculum, the sampling tool is grasped by the handling means 121 (FIGS. 15A to 15C) and is raised relative to the primary receiver 101 in which a predetermined quantity of dilution liquid is injected.

The tool 101' is then refitted into the primary receiver 101 and the inoculum is homogenized in the primary receiver 101 by successive operations of aspiration and ejection obtained by alternate sliding of the set of internal jaws 121" (FIGS. 15C, 15D and 15E). On completion of this operation, the primary receiver 101 contains a precalibrated inoculum.

The tool 101' is then extracted from the primary receiver 101 and the optical density is measured to determine the bacteria concentration of the precalibrated inoculum, allowing the volume of inoculum to be transferred into the measuring supports 104, 105 to be determined by calculation so as to supply the quantity of bacteria necessary for the proposed analysis (FIGS. 15F and 15G).

After a possible new phase of homogenization, the calculated quantity of inoculum precalibrated in the primary receiver 101 is taken by means of the tool 101' (FIG. 15H), the tool 101' then being displaced by the handling device 121 until it is positioned above or partially in the charging orifice 134 of a measuring support 104, 105 of which the stopper 150 has previously been removed, said support 104, 105 being held by a corresponding handling and transfer device 107 which has extracted said measuring support from the supporting and storage means 110.

The content of the tool 101' is then injected into the central chamber 127 of the measuring support 104, 105 under consideration by suitable sliding of the set of internal jaws 1210, ending with total immersion of the piston 115 in the body 113 and therefore with the complete emptying thereof.

Before replacing the stopper 150, a predetermined complementary quantity of dilution liquid is injected so as to obtain, in the central chamber 127, an inoculum which is perfectly calibrated with regard to the envisaged application and has the required volume.

The unit comprising primary receiver 101 and sampling and transfer tool 101' therefore allows the following different operations to be carried out:

sampling of a proportion of bacterial colony in a relatively well adjusted quantity (two sampling volumes in a ratio of about 100), automated dispersion and homogenization of this bacterial colony in a volume of water to make up a precalibrated inoculum of which the bacteria concentration is higher than the concentration desired for the calibrated inoculum, measurement of the concentration of precalibrated inoculum (number of bacteria per unit volume), pipetting of a proportion of the precalibrated inoculum and transfer thereof into a measuring support, the transferred inoculum comprising the desired number of bacteria, the transferred volume of inoculum being complemented by addition of water in the central chamber 127 of the measuring support 104, 105 under consideration, ending with a calibrated inoculum.

For the handling of the measuring supports 104, 105 and, if necessary, for their evacuation into a waste container 160 as well as that of the tools 101' and of the primary receivers 101, the apparatus according to the invention comprises, on the one hand, a first handling and transfer device 107 serving the supports 109 an d 110 and having the form of a handling arm mounted with the ability to rotate and slide on a first vertical shaft 123 and comprising two gripping jaws 124, 124' of which the first 124 is equipped with a means 125 for engagement of a primary receiver 101 and of which the second 124' has a curved shape or a hook intended to engage with two distinct points of a measuring support 104, 105 so as to hold the measuring support 104, 105 by propping it from below and by pinching in cooperation with the first gripping jaw 124 and, on the other hand, a second handling and transfer device 107' serving the incubation module 103 and the centrifugation and measuring module 106, having the form of a supporting arm mounted with the ability to rotate and slide on a second vertical shaft 123' and comprising at its free end a receiving means 125' mating with at least a part of the lower face of the measuring supports 104, 105, the two handling and transfer devices 107, 107' having an overlap zone for their respectively accessible spaces or manoeuvring zones in the region of which the measuring supports 104, 105 can in fact be transferred from one to the other.

To allow a primary receiver 101 to be gripped by the engagement means 125 of the first jaw 124, the fitted unit comprising syringe 101' and primary receiver 101 is firstly raised by the or one of the pairs of jaws 121, 121'.

The measuring supports 104, 105 charged with calibrated inoculum in the region of their central chamber 127 are brought by the second handling and transfer device 107' into the confinement enclosure containing the second and third modules 103 and 106 through a blockable aperture 161.

During the following operating phases, the measuring supports 104, 105 are repeatedly transferred between the modules 103 and 106 by means of the device 107' until the analysis is completed and the results registered by the computer unit 108.

The measuring supports 104, 105 can then be evacuated, after exploitation, into the waste container 160 using the two handling and transfer devices 107 and 107' successively.

According to a characteristic of the invention shown partially in FIGS. 7 and 8 of the accompanying drawings, the third module 106 comprises several work stations 153, in particular for measurement and centrifugation, each comprising, in addition to the various means of measurement by nephelometry, by photometry and/or by fluorimetry, on the one hand, a disc-shaped supporting base 154 carried by the upper end of a rotating vertical shaft 154' capable of engaging with interlocking or frictional holding in the concentric sleeve 151 of a measuring support 104, 105 and, on the other hand, a substantially discoidal upper pressing device 155 set into rotation round its axis of symmetry 153 by friction on the support 104, 105 arranged in the workstation under consideration, said pressing device 155 comprising one or more annular pressing members 156, 156', 156" and being able to be displaced reversibly from a high position in which said pressing members are not in contact with the measuring support 104, 105 arranged on the supporting base 154 to several lower positions in which they are successively brought to rest on the snugly fitting floating membrane 135 in a predetermined order 156", 156', 156, this membrane itself resting in the region of concentric circular or annular sealed contact zones or zones arranged in concentric circular or annular configurations with the upper wall 128 of the measuring support 104, 105 under consideration.

Depending on the type of workstation 153 under consideration, the associated pressing device 155 could comprise a variable number of pressing members 156, 156', 156".

Therefore, in the measuring stations 153, the external pressing member 156" will be absent from the associated pressing device 155.

The selection of one, two or three supporting zones in the region of the membrane 135 is made by displacing the pressing device 155 downwardly to a greater or lesser extent.

In fact, the external pressing members 156' and 156" consist of concentric annular structures which are independent of the central disc forming the pressing member 156, while being connected thereto by elastic connecting means which cause said pressing members 156' and 156" to rest against the membrane 135 when the pressing member 155 is moderately lowered.

According to the invention, a variation of the process for bacteria identification and determination of the sensitivity of bacteria to antibiotics, as described hereinbefore, can involve manually introducing a given volume of initial bacterial inoculum into a primary receiver 1 using a sampling and transfer tool (not shown), automatically carrying out definitive calibration of said inoculum in said primary receiver 1 by bringing its bacterial concentration and its volume to set values, also automatically carrying out total or partial transfer of this calibrated inoculum between said primary receiver 1 and one or more measuring supports 4, 5 intended to carry out respectively the identification, the antibiogram or these two determinations simultaneously in a single combined operation, said transfers being carried out without the initial inoculum being placed in contact with an element other than its initial receiver and its final receiver or receivers and in such a way that, at the outlet thereof, the calibrated inoculum remains confined within said measuring supports 4, 5 which are thus closed, automatically distributing the inoculum in one or more compartments 32, 45 of said measuring supports 4, 5 mainly containing appropriate reagents, carrying out, in certain cases, in particular for the antibiogram, within a measuring support 4, a so-called pre-growth operation intended to enable the bacteria to multiply rapidly before they are subjected to analysis and taking photometric measurements on the content of said compartments 32, 45 during or at the end of one or more incubations undergone by the inoculum in said measuring supports 4, 5, the measurements taken being registered by a computer 8 and being processed in order to characterize the growth of the bacteria present in the inoculum, to identify them and/or to determine their sensitivity to various antibiotics.

The concentration or density of the manually prepared inoculum has a value which is such that it is sufficient, that is that it exceeds a minimum value which can easily be checked by a skilled person. In fact, a skilled person would produce an aqueous solution and would check its density by mere observation of the appearance of said solution, experience enabling him to observe whether or not the density or concentration is adequate. Such preparation of the inoculum is readily available to a skilled person and is intended to allow subsequent adjustment or calibration to a lower final value by dilution.

According to a first characteristic of the invention, the automatic calibration of the inoculum in the primary receiver 1 involves injecting, from an initial inoculum containing a quantity of bacteria in excess relative to the reaction requirements, the excess being checked by visual observation of the turbidity of the initial inoculum, diluting water into said primary receiver 1 so as to create an increased volume of more dilute inoculum, then eliminating a proportion of the inoculum diluted in this way by aspiration until the required final volume of calibrated inoculum is obtained, these operations being carried out and optionally being repeated on the basis of optical measurements taken through the primary receiver 1 on the inoculum in order to determine the concentration thereof until the desired concentration and volume for the calibrated inoculum are both obtained.

According to a preferred embodiment of the invention, the transfer of the calibrated inoculum between the primary receiver 1 and the measuring support or supports 4, 5 is carried out by fitting all or part 11 of the primary receiver 1 containing the inoculum into a cavity provided for this purpose in each support 4, 5 so as to transfer to it the desired calibrated quantity of inoculum contained in the fitted portion of said primary receiver, this fitting ensuring the isolation necessary for the confinement of the inoculum in the unit formed by the measuring support 4, 5 and the primary receiver 1 or the part 11 of the primary receiver 1 fitted in said support 4, 5 as well as the closure of this unit.

During automatic operation and without intermediate handling by an operator of the primary receiver 1 and of the supports 4 and/or 5, all these elements are introduced at the beginning by the operator into a first storage and preparation module 2 in which the supports 4 and/or 5 are supplied with inoculum, each by means of at least one receiving chamber provided in said supports, from the primary receiver 1 or directly by means of it.

After the supports 4 and/or 5 have been supplied in this way, the inoculum is equally distributed in the compartments thereof by centrifugation, then said rotating supports 4 and/or 5 are transferred into a second incubation module 3 from which they are extracted periodically and are subjected to nephelometric and/or photometric and/or fluorimetric measurement in the module 6 for identification and/or production of antibiograms.

In the scope of this variation of the process according to the invention, the operations of pre-growth of the inoculum, distribution of the inoculum in the measuring compartments, determination of the beginning of pre-growth, transfer of the inoculum after completion of pre-growth and photometric measurement of the measuring supports, are carried out in a manner similar to that described hereinbefore with reference to the first variation, their practical implementation and the means, devices and apparatus used being different, as will be demonstrated by the following description.

To prevent contamination of the calibrated or uncalibrated inoculum present in the antibiogram measuring support 4, the passage from the pre-incubation state to the incubation stage is carried out without breaking the confinement of the interior of the rotating measuring support concerned 4 relative to the exterior, said support remaining closed and said passage being brought about by an action such as a push on a blocking element participating in the production of this confinement.

Furthermore, if the initial inoculum does not contain sufficient bacterial material, the stage of automatic calibration can be omitted according to a slightly modified version of the variation of the process described hereinbefore.

An initial bacterial inoculum which has been manually positioned is therefore introduced automatically by a suitable sampling and transfer tool into a primary receiver 1', in a measuring support as mentioned hereinbefore and intended to carry out either an antibiogram or simultaneous combined analysis for identification and antibiogram, said automatic introduction being carried out or completed in such a way that the measuring support is closed and insulated from the exterior at the outlet thereof.

The primary receiver 1' will have an external configuration and bulk identical to the primary receiver 1 and will comprise a container for the storage and handling of the initial bacterial inoculum known as a macropipette 73 allowing the transfer of its content from said primary receiver 1' into the target combined antibiogram or determination measuring support.

After this introduction of the initial bacterial inoculum into said measuring support, the process involves automatically distributing an aliquot part of the initial inoculum in one or more compartments 37, 45 containing no reagents, of said measuring supports 4, 5 then carrying out pre-growth of this initial inoculum within the measuring support 4, 5 as mentioned hereinbefore, enabling the inoculum bacteria to multiply rapidly by a first incubation or pre-incubation during which photometric measurements intended to measure the concentration of the bacterial inoculum are carried out in the region of the compartment or compartments 37, 45 containing said first aliquot part of the inoculum, then automatically distributing the remainder of the inoculum in the other compartments 32, 45 containing reagents, by centrifugation and taking photometric measurements on the inoculum in the region of said compartments 32, 45, as described above during a new incubation phase undergone by the inoculum in said measuring supports 4, 5, the measurements taken being registered by a computer 8 and being processed in order to characterize the growth of the bacteria present in the inoculum, to identify them and/or to determine their sensitivity to various antibiotics.

The variation of the process according to the invention will now be described in detail with reference to a practical embodiment and in conjunction with a description of the materials used.

Figure 18:
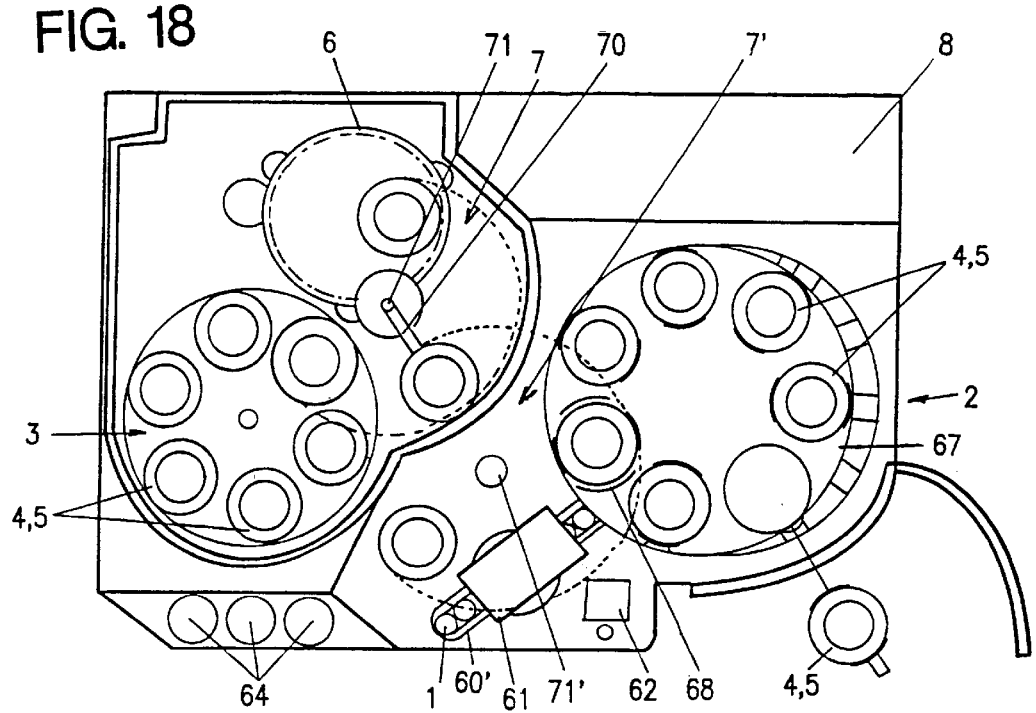
FIG. 18 is a view similar to that in FIG. 17 of the apparatus on a higher level.
Figure 17:
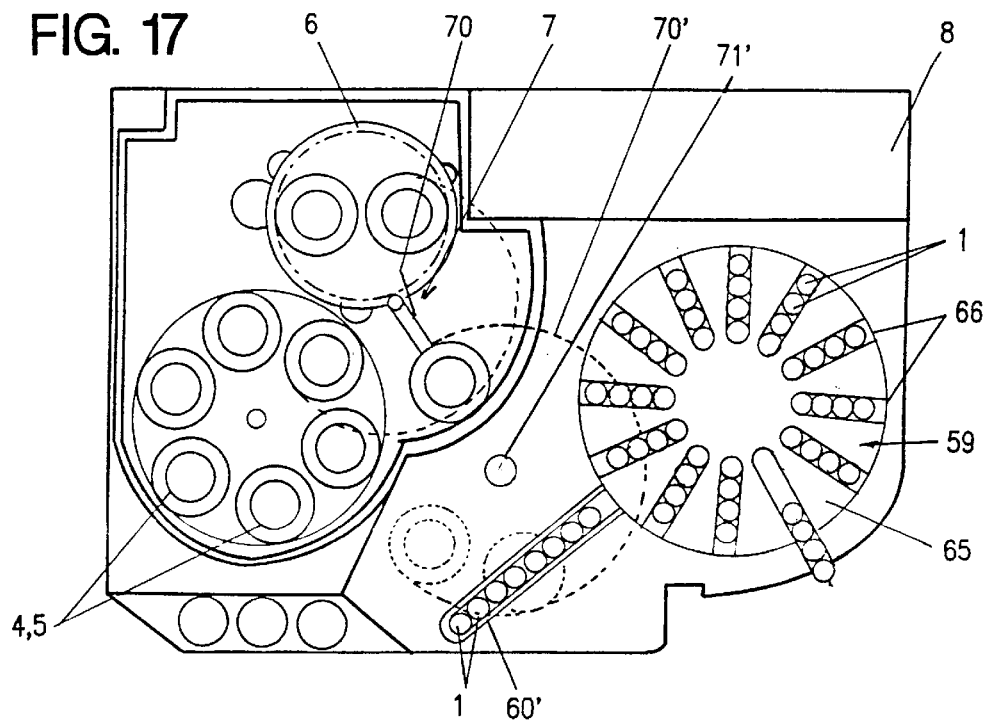
FIG. 17 is a plan view in section at a lower level of the apparatus according to claim 16.

An apparatus for carrying out the variation of the process is shown more particularly in FIGS. 16 to 18 of the accompanying drawings and essentially consists of a first module (2) for receiving, storing and preparing fresh and worn measuring supports 4 and/or 5, of a second module 3 for incubation of the supports 4 and/or 5, of a third module 6 for nephelometric and/or photometric measurement, of a transfer device 7, 7' serving the modules 2, 3 and 6 and of a computer 8 for monitoring and controlling the various stages of the process and for acquiring, registering, processing, evaluating and/or restoring data.

According to the invention, the first module 2 for receiving and storing and preparing fresh and worn measuring supports 4 and/or 5 also comprises at least one means 59 for receiving and storing primary receivers 1 containing the non-calibrated bacterial inoculum and a device 60, 61 for calibration of the inoculum in said primary receivers 1 and for preparation of said measuring supports 4 and/or 5.

Figure 19:
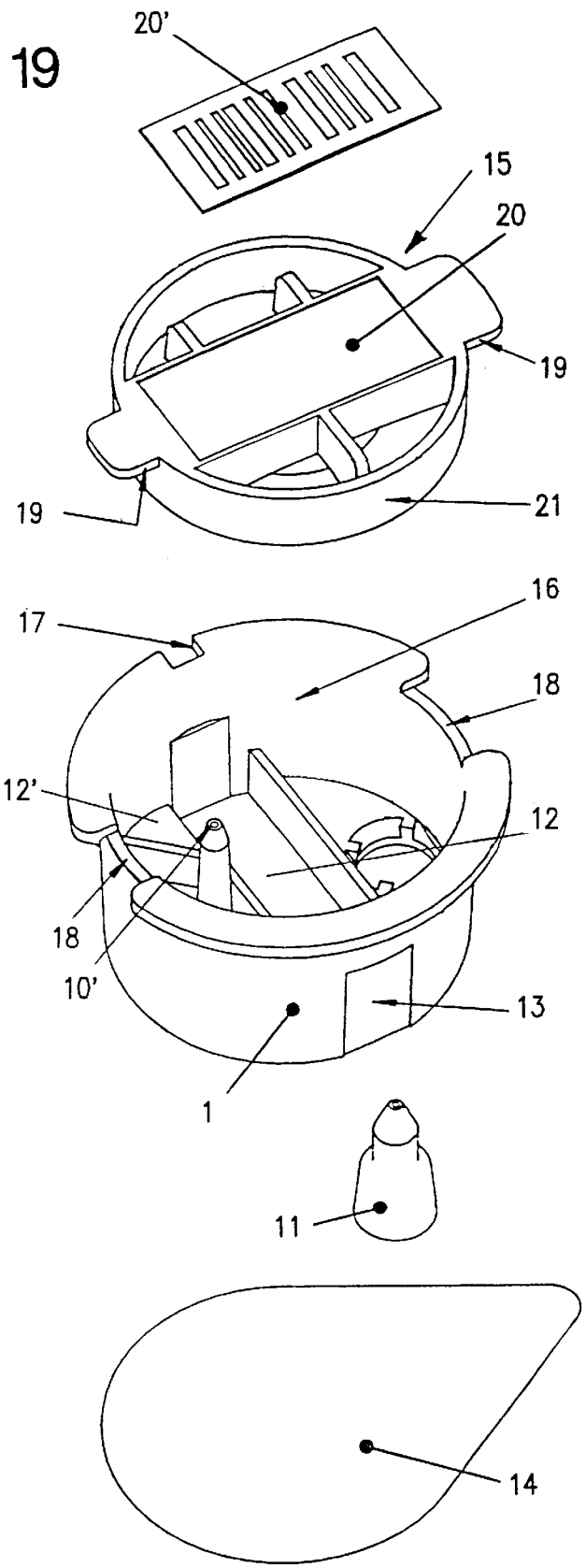
FIG. 19 is an exploded perspective view of a primary receiver according to a variation of the invention corresponding to the apparatus in FIG. 16.
Figure 20:
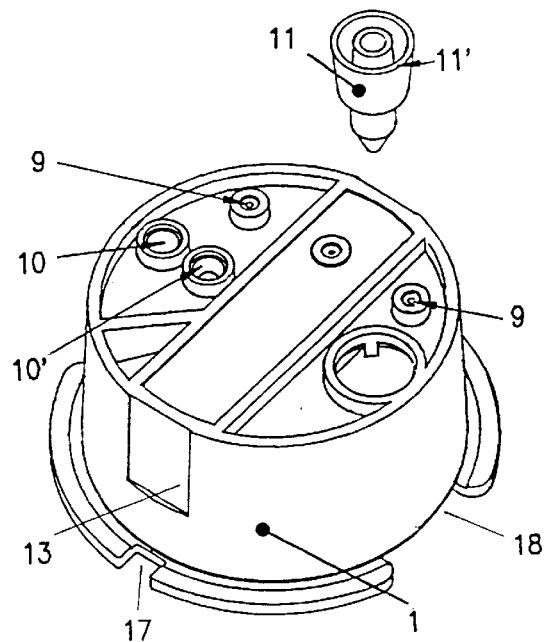
FIG. 20 is a perspective view through the bottom of the primary receiver shown in FIG. 19.

According to a characteristic of the invention, each primary receiver 1 for receiving the inoculum advantageously (FIGS. 19, 20) has the form of a cylindrical receiver equipped on its bottom with at least one vent tube 9, with an overflow evacuation conduit 10, optionally with a conduit 10' for setting a lower volumetric level of inoculum, with a means for sampling a predetermined quantity of inoculum mounted separably by tearing or fitting in the bottom of the receiver 1 and eccentric relative to the axis of said receiver 1 such as a pipette 11 and with a trough-shaped transverse recess 12 extending between the walls of the receiver 1, which is provided at each end of said recess 12 with a measuring window 13, this recess 12 also being equipped with a raised part 12' communicating with said recess 12, the vent 9, the overflow conduit 10, the lowering conduit 10' and the sampling means 11 being closed in a sealed manner by a tearable film 14, a closure cover 15 cooperating by sealed conical fitting with the upper conical part 16 of said receiver 1.

The transverse recess 12 and, more particularly, the raised part 12' thereof is designed for the manual preparation of the inoculum in aqueous solution from a culture solution, said solution being deposited in the bottom of the recess 12 on the raised part 12' by means of a sampling member serving simultaneously to produce a first mixture of the culture solution with the added water.

The conical upper part 16 of the primary receiver 1 is provided with at least one shallow notch 17 and with two deeper notches 18 of different widths arranged in alignment with one another and at 90° to the axis passing through the shallow notch or notches 17, this or these shallow notches 17 being aligned in the axis of the recess 12 of the bottom and the deeper notches 18 cooperating with tabs 19 of corresponding section provided on the sealed closure cover 15 provided, on the one hand, on its upper face with a surface 20 extending in the axis of the tabs 19 and, on the other hand, with a conical wall 21 having a shape corresponding to that of the conical upper part 16 of the receiver 1 and connecting the tabs 19.

The slightly retracted surface 20 extending between the tabs 19 and therefore between the notches 18 when the closure cover 15 is mounted on the primary receiver 1 is designed to receive a coded identification means 20' such as an adhesive label with a bar code.

The shallow notch 17 allows precise positioning of the primary receiver 1 in the module 2 so as to allow, in particular, reading of the identification means. This notch 17 is also intended to ensure the correct orientation of the primary receiver 1 during the automatic calibration of the inoculum as well as for the inoculation of the rotating support 4 for producing antibiograms.

The pipette 11 forming the means for taking a predetermined quantity of inoculum is mounted separably by tearing or by fitting in the bottom of the receiver 1 inverted so as to present its downwardly turned cover 15. This pipette 11 is provided, close to its end projecting beneath the bottom of the receiver 1, with a collar or a sleeve 11' by which it is connected to the bottom of the receiver 1 in the region where this bottom is traversed, for example by an embrittled sealed connection or by fitting. In a known manner, the bottom and the lateral walls as well as the cover 15 of the primary receiver 1 are produced by moulding from a synthetic material. Thus, during the filling of the receiver 1 and during the handling thereof, the seal in the region of the pipette 11 is ensured whereas, after inversion of the receiver 1 closed by the cover, during engagement of the pipette 11 and by a slight push on it, it is disconnected from the bottom of the receiver 1 and can be transferred for use after aspiration of a predetermined quantity of inoculum.

Figure 21:
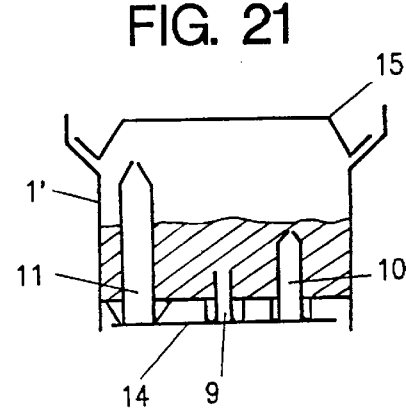
FIGS. 21 to 23 are schematic sectional views showing the primary receiver in FIG. 19 during the successive stages of preparation of the inoculum.
Figure 22:
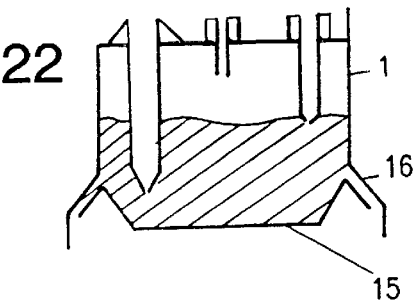
Figure 23:
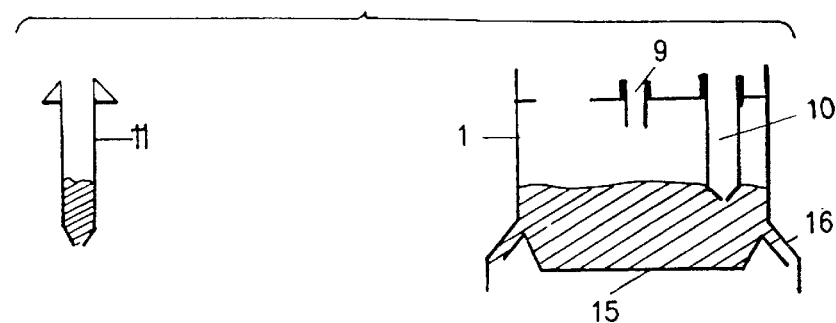

FIGS. 21 to 23 show schematically the successive stages of preparation of the inoculum and verification of its minimum density in the receiver 1 then the sealed closure thereof by the cover 15, the tearable film 14 hermetically closing the external orifices of the vent tube 9, of the evacuation conduit 10 and of the pipette 11. During introduction of the primary receiver 1 into the first module 2 for reception and storage as well as calibration of the inoculum, the receiver 1 is inverted so as to have its bottom turned up and the film 14 is torn to allow the calibration of the inoculum by possible adjustment of its volume and/or by elimination of the overflow by means of the device 60, 61 for calibration of the inoculum and preparation of the rotating supports 4 and/or 5.

Figure 26:
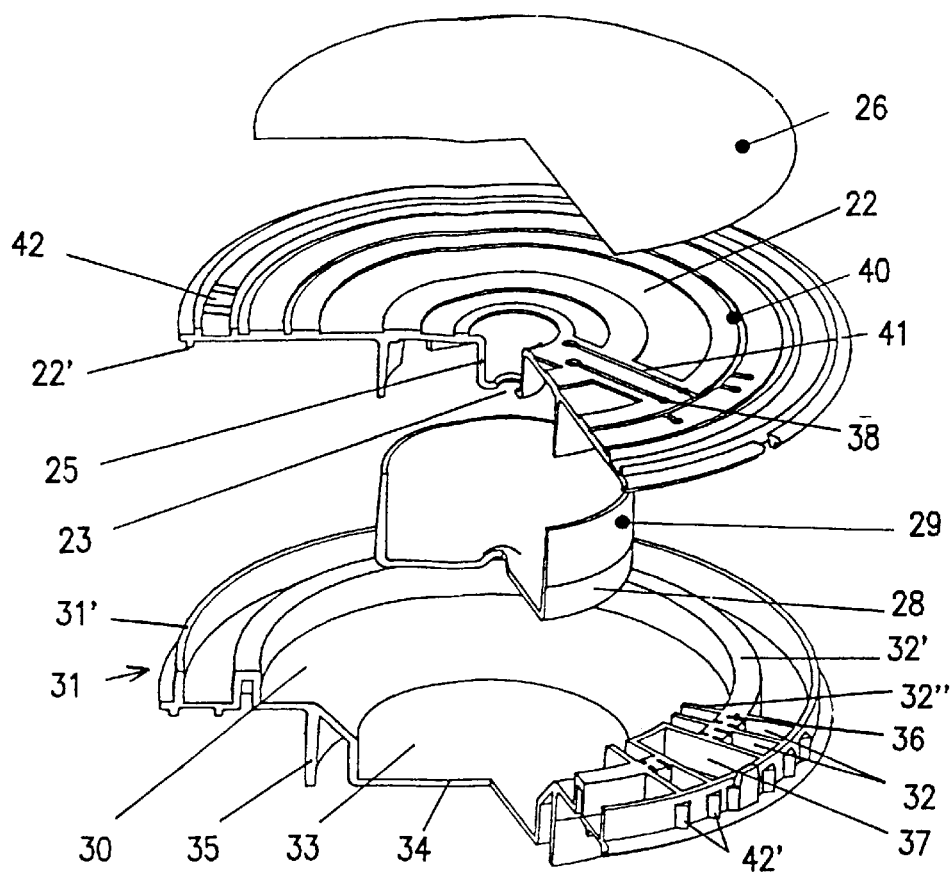
FIG. 26 is a view similar to that in FIG. 24 showing a measuring support for antibiogram intended to be used in the apparatus shown in FIGS. 16 to 18.
Figure 27:
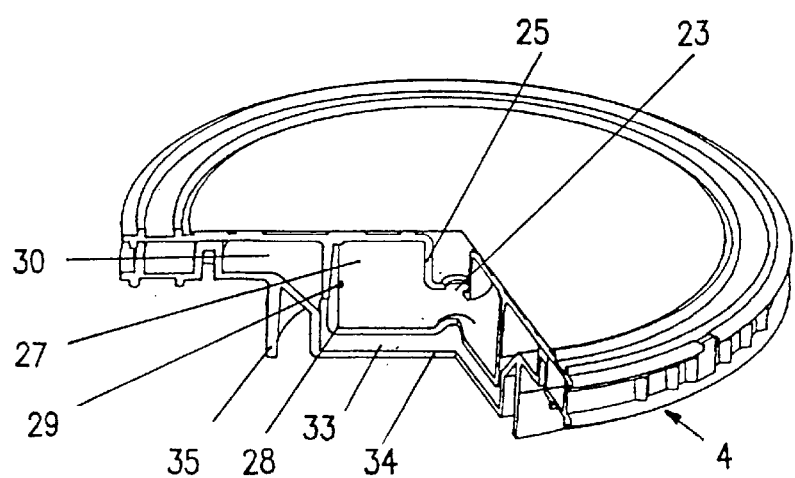
FIG. 27 is a partially broken away perspective view of the support according to FIG. 26 prior to inoculation.
Figure 28:
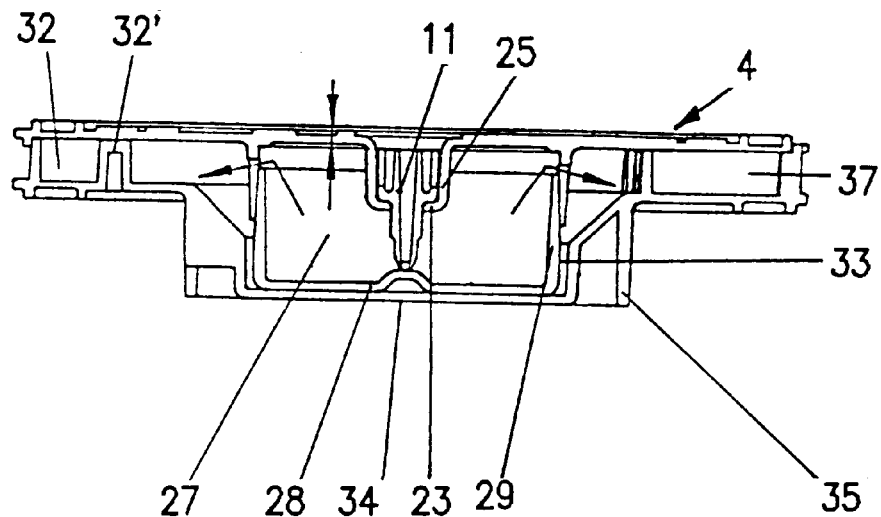
FIG. 28 is a view similar to that in FIG. 25 showing the measuring support for antibiogram in the position for distribution of the inoculum in the compartments.

The rotating support 4 for antibiogram shown in FIGS. 26 to 28 of the accompanying drawings advantageously has the form of an upper composite disc provided with peripheral compartments 32 for receiving the inoculum and antibiotic preparations and is characterized in that it is provided with a concentric cylindrical body having a smaller diameter than the disc and connected to said disc, forming a central chamber 33 for receiving the inoculum for distribution by centrifugation, said chamber 33 being supplied through an orifice 23 in the upper face of the upper composite disc and being surrounded by a sleeve 35 for gripping and rigidifying the unit.

The upper composite disc of the rotating support for antibiogram 4 consists, on the one hand, of a circular cover part 22 provided with an orifice 23 in its centre and, on the other hand, of a circular plate 31 of which the upper face turned toward the lower face of the cover part 22 carries, in relief on its periphery, compartments 32 for receiving the inoculum and antibiotic preparations, this circular plate 31 being connected to the concentric chamber 33 closed by a bottom 34, the cover part 22 being provided with a rim 22' extending concentrically above a circular wall 31' of the circular plate 31, limiting compartments in relief 32 toward the exterior and fixed to said circular wall 31' by adhesion or welding.

According to a characteristic of the invention, the circular plate 31 of the lower body part is provided, between the compartments in relief 32, with at least one pre-incubation compartment 37 connected, by means of a capillary tube 38, to a concentric chamber 27 made beneath the circular plate 22 of the cover part in the concentric chamber 33 of the circular plate 31 forming the lower body part.

The orifice 23 provided in the centre of the cover part 22 is arranged in a pit 25 extending concentrically within the concentric chamber 27 having a moving dish 28 provided with a dry culture medium, said moving dish 28 having a sealed guide wall 29 limiting a basin with said moving dish 28, the pit 25 being closed by a sealed film 26 covering the upper part of the circular cover plate and simultaneously limiting the capillary tube 38.

The sealed guidance of the dish 28 by means of its wall 29 can be achieved by lightly gripped sliding mounting of said dish 28 and its wall 29 in the concentric chamber 27. The moving dish 28 is designed for the preparation of the culture arranged on its bottom, this preparation being carried out in the form of an aqueous solution which is then dried, the wall 29 accommodating the aqueous solution until it has dried completely.

The compartments in relief 32 are limited on their face turned toward the interior of the rotating support 4 by a concentric circular wall 32' and are each provided, on the face of said concentric wall 32' opposed to the compartments 32, with vertical baffles 32" determining means for sensing the inoculum during centrifugation.

Figure 24:
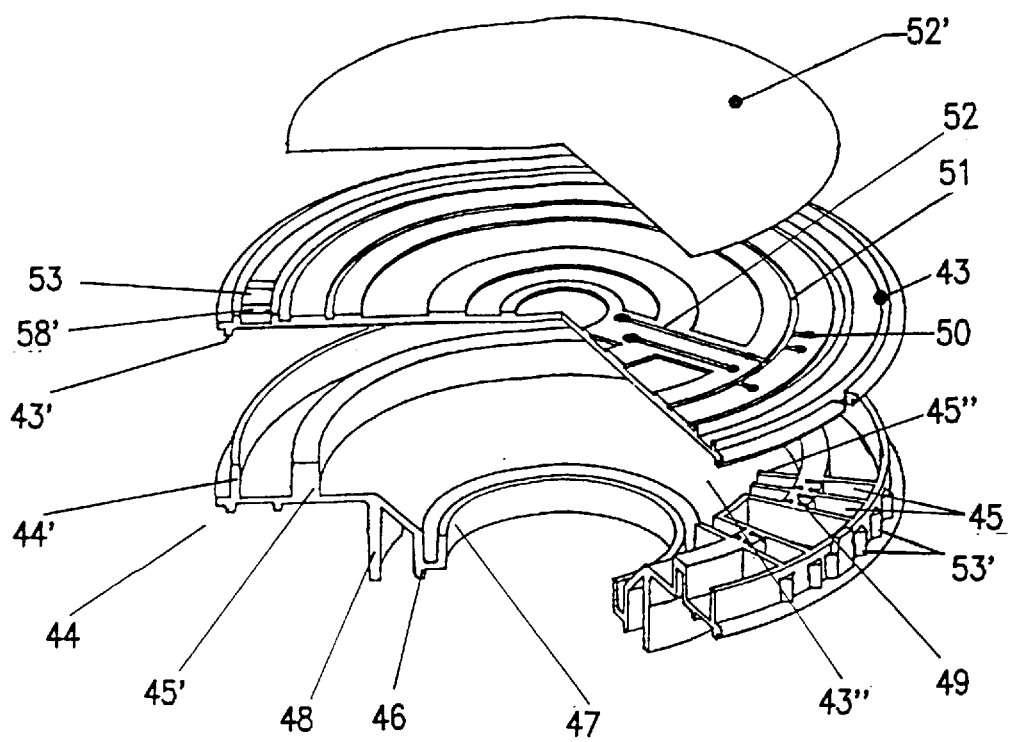
FIG. 24 is an exploded perspective view, partially broken away, of a measuring support for identification intended to be used in the apparatus shown in FIGS. 16 to 18.
Figure 25:
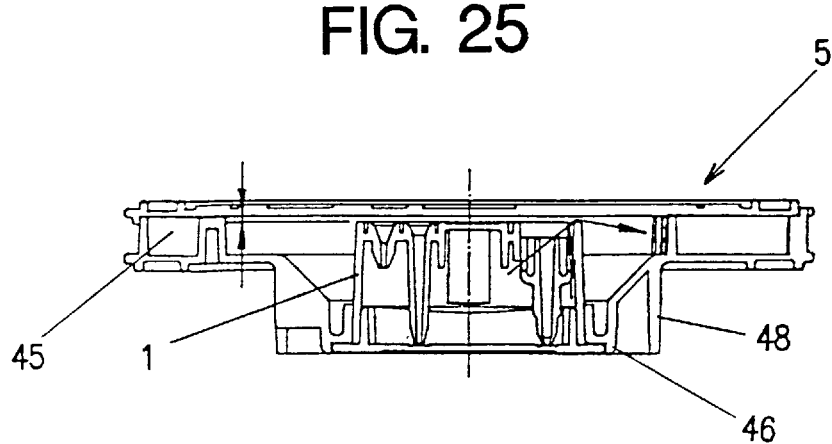
FIG. 25 is a section of the measuring support shown in FIG. 24 for identification provided with an associated primary receiver.

The rotating support 5 for identification shown in FIGS. 24 and 25 of the accompanying drawings also advantageously has the form of an upper composite disc provided with peripheral compartments 45 for receiving the inoculum and characterizing reagent, and is characterized in that it is provided with a concentric cylindrical body of smaller diameter than the disc and connected to said disc, forming a concentric sleeve 46 for receiving the primary receiver 1 in the inverted position for the distribution by centrifugation of the inoculum, said sleeve 46 being surrounded by a concentric sleeve 48 for gripping and rigidifying the unit.

The concentric sleeve 46 extends, at the centre, beneath the lower face of the circular plate 44, is connected to it and is equipped at its free end with a part of conical wall 47 extending internally to said sleeve 46 and intended to cooperate with the external wall of the conical upper part 16 of the primary receiver 1.

The upper composite disc of the rotating support for identification 5 consists, on the one hand, of a circular cover part 43 and, on the other hand, of a lower part in the form of a circular plate 44 provided, on its upper face turned toward the lower face of the cover part 43 in relief on its periphery, with compartments 45 for receiving the inoculum and characterizing reagents, the cover 43 being provided with a rim 43' extending concentrically above the circular wall 44' of the circular plate 44 limiting compartments in relief 45 toward the exterior and fixed to said circular wall 44' by adhesion or welding.

The compartments in relief 45 are limited on their face turned toward the interior of the rotating support 5 by a concentric circular wall 45' and are each provided, on the face of said concentric wall 45' remote from the compartments 45 with vertical baffles 45" determining the means for sensing the inoculum during centrifugation.

The means for sensing the inoculum 45" during centrifugation provided, as viewed in the radial direction, in front of each compartment 32, 45 respectively with supports 4 and 5 are each connected to the interior of a corresponding compartment 32, 45 by means of a capillary tube 36, 49 and are open furthermore into an internal space 30, 43" communicating with the concentric chamber 33 of the circular plate 31 forming the lower body part or with the space for receiving the primary receiver 1 in the concentric sleeve 46 extending beneath the lower face of the circular plate 44 forming the lower part of the composite disc, the compartments in relief 32, 45 being connected furthermore, each by means of a radial capillary tube 39, 50, to a circular capillary tube 40, 51 opening, via a further capillary tube 41, 52, to the exterior of the circular cover plate 22 or of the circular cover part 43, the pre-incubation compartment 37 provided on the measuring support 4 for antibiogram being connected directly, by a corresponding passage hole, to the circular capillary tube 40. These various capillary tubes are limited in the upper part of the circular plate 22 and of the cover 43 by the sealed film 26 or 52', the capillaries 41 and 52 communicating at their end closest to the central axis of the discs 31 and 44 with the internal chambers 27 and 43" by holes pierced in the circular plates 22 and 43.

A sealing film 26, 52 can have, in particular in a known manner, the form of a self-adhesive film made of two materials, for example of aluminium and polyethylene. Thus, during the successive filling by centrifugation of the pre-incubation compartment 37 and the relief compartments 32, 45 by means of the respective capillaries 38, 36 and 49, the air contained in said compartments can escape in compensation for the filling through the capillary tubes 39, 50, 40, 51 and 52 toward the chambers 27 and 43".

The circular cover plate 22 and the circular cover 43 are also equipped, above each compartment 32, 45 and close to its edge, with a measuring window 42, 53, a similar window 43, 54 being provided beneath the lower face of the circular plate 31, 44 forming the lower part of the body or of the composite disc opposite each measuring window 42, 53 and at least one indexing reflective zone 42', 53', formed on the external face of the external peripheral wall of the supports 4, 5, being associated with each compartment 32, 45 with an angular offset which is fixed relative thereto.

Thus, during measurements, the passage of each compartment in front of the measuring device is perfectly marked during the rotation of the rotating support 4 or 5 owing to the reflective zones or indexing mirrors and the corresponding measurement can be taken in a perfectly synchronized manner.

Figure 29:
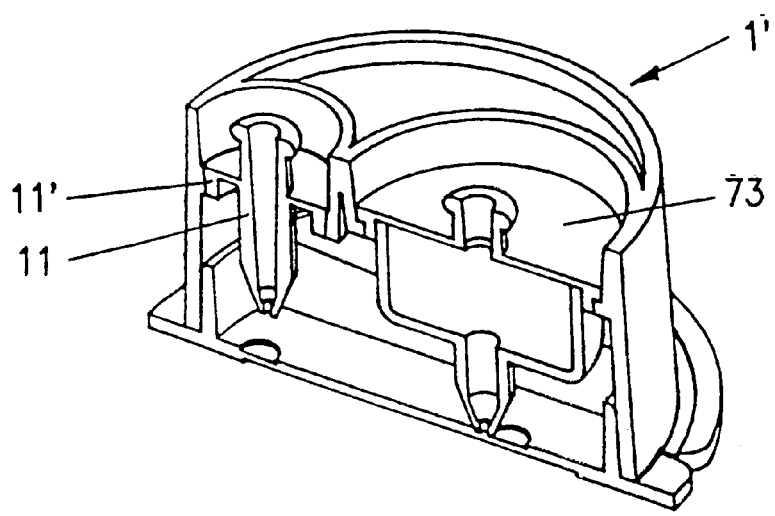
FIG. 29 is a perspective view in section of a variation of the primary receiver shown in FIG. 19 for the treatment of a low volume bacterial substance without automatic calibration.

The primary receiver 1' used for the automatic introduction of an initial bacterial inoculum into a measuring support for antibiogram or simultaneous combined analysis advantageously has the form, as shown in FIG. 29 of the accompanying drawings, of a container provided, on the one hand, with a pipette 11 identical to that associated with the primary receiver 1 and, on the other hand, a macropipette 73 for transferring the total content of the receiver 1', this macropipette being able to be detached from the primary receiver 1', being used to empty its content into the support 4 and then being replaced in the primary receiver 1', the pipette 11 then being detached and used to block the support 4 while being deposited in the pit 25. In such a case, the solution is arranged directly in the macropipette 73 and not in the receiver 1', the pipette 11 being used only as a blocking stopper for a support 4 for antibiogram or possibly for an addition of water.

As shown by the schematic FIGS. 21 to 23 of the accompanying drawings, the inoculation of a rotating support 4 for antibiogram is carried out by grasping, by means of a gripping member of a device 64 for pipetting and for injection of water and gas from the end of the pipette 11 passing beyond the bottom of the receiver 1, then by introduction of said pipette 11, after perforation of the sealed film 26, in the pit 25 extending concentrically to the interior of the concentric chamber 27 so as to free the axis thereto. The inoculum can thus be poured into the concentric chamber 27 and an additional contribution of water can be made. In the chamber 27, the inoculum mixes with the dry culture medium intended to supply its growth.

The pipette 11 is therefore immersed through the orifice 23 and the pit 25 and guided in them by means of its sleeve or collar 11' until it abuts against the moving dish 28 with its free end so as to provide a seal from the exterior. After stirring to promote homogenization of the content of the dish 28, a first centrifugation process is carried out so as to bring a proportion of said content into the pre-incubation compartment 37 through the capillary tube 38.

As soon as the beginning of growth has been observed by nephelometric measurement, the rotating support for antibiogram 4 will be subjected to a new centrifugation process, the moving bottom 28 of the concentric chamber 27 being previously pushed by means of the pipette 11 so as to clear, between its wall 29 and that of said chamber 27, passages allowing the pouring of the inoculum into the concentric chamber 33. The rotating support 4 will therefore be displaced successively into the measuring module 6 and into the second incubation module 3 for nephelometric measurement and incubation.

The rotating support 5 for identification can be inoculated immediately after inoculation of the support 4 by transfer of the primary receiver 1 beneath a support 5 and tight fitting in said support 1. To this end, the part of internal conical wall 47 of the concentric sleeve 46 grips the external wall of the conical upper part 16 of the receiver 1 and seals the assembly. centrifugation of the rotating support 5 therefore has the effect of bringing the inoculum contained in the receiver 1 into the space limited above this receiver 1 beneath the cover part 43 through the orifice made by tearing or the retraction of the pipette 11 and of its sleeve or collar 11' and, from there, toward the compartments 45 through the capillaries 49, the excess air being evacuated through the capillaries 50 to 52. The photometric measurements are taken after incubation with the characterizing reagents.

As shown more particularly in FIGS. 16 to 18 of the accompanying drawings, the automatic calibration device consists, on the one hand, of a lower unit 60 comprising, in particular, a means for reading the coded identification means attached to the transverse groove 20 of the cover 15 of the primary receivers 1 and a means of measuring the optical density of the inoculum present in said receivers 1 and, on the other hand, of an upper unit 61 essentially comprising a device for pipetting and for injection of water and air.

This device can on the one hand be provided with a gripping member which is movable at least in a vertical direction and with an overflow evacuating device and can, on the other hand, be connected to a pumping or aspiration means 62, to a set 63 of valves for controlling the flows of liquid and air and to liquid and air receivers 64.

The gripping member of the pipetting device can mate in a sealed manner with the free external end of the pipette 11 of a receiver 1 when the receiver 1 is arranged at a suitable position known as the working position.

This gripping member will also carry out the injection of water during the automatic calibration phase as well as the detachment of the pipette 11 by tearing or release of the bottom of the primary receiver 1, the holding of the pipette 11 in a retracted position with retention of the inoculum and the introduction of said pipette into the rotating support 4 for antibiogram with injection of the inoculum.

Said pipetting device could alternatively be connected to an aspiration means and to a means for the controlled injection of a quantity of fluid, in particular water or air, extracted from corresponding reservoirs.

The upper unit 61 could also comprise a moving joint for the sealed connection of an overflow pipe or of a pipette connected to a continuous aspiration means and a recovery reservoir and said moving joint or said pipette could engage with the external free end of the overflow evacuation conduit 10 and/or of the levelling conduit 10' integrated in the bottom of the primary receiver 1 when the primary receiver 1 is positioned in the region of the workplace.

As also shown in FIGS. 16 to 18 of the accompanying drawings, the receiving and storage means 59 consist of at least one disc 65 which can be set into rotation in a controlled manner and can be provided with a plurality of storage grooves 66 arranged along the radii of said disc 65 and each capable of containing, either directly or by means of an intermediate carrier, an aligned row of primary receivers 1 in an inverted position and indexed in an angular position round their central axis of symmetry, each of said grooves 66 being able to be brought individually opposite the aperture of the automatic calibration device 60, 61 by mere rotation of said disc 65 for the extraction of the row of primary receivers 1 under consideration.

The intermediate carriers can also advantageously each consist of a profiled elongate container 60' which can each simultaneously contain a plurality of primary receivers 1 in the form of a row of primary receivers 1 in inverted positions of which each one is indexed in an angular position round its central axis of symmetry and can be positioned individually at a defined working position in the region of the upper units 61 and lower units 60 constituting the automatic calibration and preparation device.

Each primary receiver 1 can thus be brought individually and positioned vertically in the region of the workplace by mere sliding of the profiled elongate container 60'.

Furthermore, the radial guidance of the profiled elongate containers 60' forming carriers for the rows of primary receivers 1 in the storage grooves 66 of the means 59 will allow stirring of the contents of all said primary receivers 1 by successively subjecting each of said rows, each arranged in one of said carriers 60', to a reciprocating to-and-fro movement.

According to a further characteristic of the invention, the transfer devices serving the various modules 2, 3 and 6 comprise, in particular, on the one hand, a first conveying member 7 ensuring, in particular, the transfer of the rotating supports 4 and 5 between the incubation modules 3 and measuring modules 6 and the takeover thereof from the automatic calibration device 60, 61 and on the other hand a second conveying member 7' ensuring the takeover and deposition of a rotating support 4 or 5 in the region of a corresponding storage magazine 67, the transfer and holding thereof in the automatic calibration device 60, 61 and its travel to a predetermined position allowing it to be taken over by the first conveying member 7.

The transfer movements of rotating supports 4, 5 can obviously also be carried out in the opposite direction in order to sort the worn supports 4, 5 of which exploitation is completed. In this case, each worn support 4, 5 will be transmitted by the first conveying member 7 to the second conveying member 7' which will bring it to the storage magazine 67 of the first module 2 where it will be discharged and sorted into one or two positions provided for this purpose.

As also shown in FIGS. 16 to 18 of the accompanying drawings, the storage magazine 67 is located in the upper part of the first module 2 and consists of a circular magazine which can be set into rotation and comprises a plurality of batches of measuring supports 4, 5 which are fresh and worn in their peripheral region.

Each batch can be brought individually into the gripping zone of the conveying member 7' allowing the conveying member 7' to raise the upper measuring support 4, 5 from a suitably positioned batch and to transfer it to the automatic calibration device 60, 61.

Obviously, said conveying member 7' could also receive a worn measuring support 4, 5 brought by the first conveying member 7 to the changeover position and could deposit it in a corresponding batch, previously positioned at the suitable point served by said second conveying member 7'.

According to a preferred embodiment of the invention, the handling member of the second conveying member 7' can have the form of a gripper 68 and said gripper 68 can be positioned, in particular, between the lower units 60 and upper units 61 of the automatic calibration device in such a way that the measuring support 4 or 5 carried by it is arranged in the region of the workplace of said automatic calibration device.

The measuring supports 4 and 5 are held by said gripper 68 by gripping in the region of their upper part.

The positioning of the supports 4, 5 in the region of the workplace of the automatic calibration device 60, 61 will allow the pipette 11 to be introduced into a measuring support 4 for antibiogram or the fitting of a primary receiver 1 in a measuring support 5 for identification.

The first and second conveying members 7 and 7' can each advantageously consist of a supporting arm 70 and 71 respectively mounted with the ability for rotation and vertical translation on an axis 71 and 71' respectively integral with the frame of the apparatus.

The movements of the first conveying member 7 of which the axis can be fixed on the measuring module 6 and of which the handling member can consist of a supporting plane allow the charging or discharging of a measuring support 4 or 5 from or toward the second conveying member 7', the incubation module 3 and the measuring module 6.

The measuring module 6 can comprise, in the region of its access aperture, an exchange mechanism transferring the measuring supports 4, 5 between a charging/discharging position accessible to the conveying member 7 and a measuring position, by interchanging two measuring supports 4, 5 between these two positions.

In a preferred manner and in order to increase the efficiency of the apparatus, the period required to replace a support 4 or 5 after the phase of measurement and supply of a new support 4 or 5 in the region of the measuring module 6 is almost identical to the duration of the measuring phase.

Furthermore, the measuring supports 4, 5 can be centred and set into rotation in the region of the measuring position of the measuring module 6, said measuring supports 4, 5 being set into rotation by means of an upper retractable member.

To be able to carry out centrifugation at high speed for rapid distribution of the inoculum in the peripheral compartments of the measuring supports 4, 5, the measuring module 6 can comprise a distinct additional centrifugation device 72 which can be served by the first conveying member 7.

The modules 3 and 6 are advantageously situated in a confined chamber and are advantageously thermally regulated to a temperature favourable to incubation whereas the storage magazine 67 of the supports 4, 5 is at ambient temperature or is located in an optionally cooled space.

The confined thermally regulated chamber could comprise, in the region of the exchange link between the first conveying members 7 and the second conveying members 7' an aperture which is blockable, optionally in a sealed manner, and is controlled by the control and monitoring computer 8.

The apparatus for carrying out the process according to the invention is consequently composed of a limited number of constituent parts of which the movements, in particular in the region of the transfer means and of the automatic calibration device are extremely simplified. Furthermore, the specific structure and internal arrangement of said apparatus produces minimum bulk for a given processing capacity.

The invention is obviously not limited to the embodiments described and illustrated in the accompanying drawings. Modifications are possible, in particular with regard to the constitution of the various elements or by substitution of technical equivalents, without departing from the scope of protection of the invention.

What is claimed is:

1. An apparatus for determining the identity and antibiogram of bacteria, said apparatus comprising:

primary receivers;

measuring supports;

a first fresh module constructed for supporting and storing said measuring supports and said primary receivers, said first fresh module arranged for said primary receivers and said measuring supports being located for cooperating operation with a corresponding sampling and transfer tool;

a second module arranged to accept measuring supports from said first fresh module, said second module being adapted for the incubation of the accepted measuring supports;

a third module in measuring support communication with said second module, said third module providing centrifugation and at least one of nephelometric, photometric, and fluorimetric measurement of said accepted measuring supports received from said second module;

a transfer and handling device serving said first, second and third modules for the transfer of measuring supports;

a confinement enclosure surrounding said second module and said third module;

a crown-shaped supporting means carrying said primary receivers, said crown-shaped supporting means extending concentrically around and beneath a disc-shaped supporting means bearing said measuring supports, said crown-shaped supporting means and said disc-shaped supporting means being mounted to rotate around a same axis;

said crown-shaped supporting means arranged such that rotation of said crown-shaped supporting means brings each primary receiver into a region of a station for handling of an associated sampling and transfer tool and for an optical density measurement of a content of a positioned primary receiver; and a computer for monitoring and acquiring, registering, processing, evaluating and storing data.

2. An apparatus according to claim 1, wherein:

each said primary receiver comprises a given volume, a cylindrical receiver form open in a radial rim region of an upper part, said radial rim being adapted for holding said primary receiver in one of a corresponding recess in said crown-shaped supporting means; and each said sampling and transfer tool comprises a syringe with a body comprising a frontal tapered part adapted for sampling and ejection and a substantially cylindrical rear part adapted for storage and gripping, said rear part having at least one external radial offset in a region of an end adjacent to said frontal part adapted for partial fitting and blocking of said body in one of said primary receivers, wherein with said sampling and transfer tool in a fitted and blocking position in said one primary receiver, a front free end of said frontal part is located in adjacent proximity to a bottom of said one primary receiver.

3. An apparatus according to claim 1, wherein the syringe further comprises, in a region of said front end, a means for sampling a quantity of bacterial colony, by volume, as a function of a positioning of a piston interior to said rear part.

4. An apparatus according to claim 1, wherein each primary receiver comprises two opposing measuring windows adapted to measure the optical density of the content of said each primary receiver at said station, said two opposing measuring windows being located in a lateral wall in a vicinity of a bottom of said each primary receiver.

5. An apparatus according to claim 1, further comprising a syringe transfer tool located in a region of said station, said transfer tool comprising:

two external jaws constructed to engage in a rigid, blocking manner a radial rim of said sampling and transfer tool in a region of an aperture of a rear part of a body of said sampling and transfer tool; and two internal jaws arranged concentrically between said two external jaws and constructed to engage in a rigid and blocking manner with a swelling of an actuating rod of said sampling and transfer tool, wherein said internal and external jaws are constructed to be closed simultaneously by sliding a sleeve around and along said external jaws, said internal jaws being able to slide relative to said external jaws and relative to said sleeve, and wherein said sleeve is able to rest on said crown-shaped supporting means and on a radial edge of an upper aperture of an associated primary receiver to block said associated primary receiver within an associated recess of said crown-shaped supporting means during the sliding of said internal or external jaws.

6. An apparatus according to claim 1, further comprising:

a first handling and transfer device serving said crown-shaped and disc-shaped supporting means, said first handling and transfer device comprising a handling arm mounted to rotate and slide on a first vertical shaft, a first gripping jaw equipped with a means for engagement of one of said primary receivers and a second gripping jaw with a curved shape or a hook engagable with two distinct points of an associated measuring support so as to hold the associated measuring support by propping the associated measuring support from below and by pinching in cooperation with the first gripping jaw, and a second handling and transfer device serving the second module and the third module, said second handling and transfer device comprising a supporting arm mounted to rotate and slide on a second vertical shaft, and at a free end, a receiver mating with at least a part of a lower face of the measuring supports, the first and second handling and transfer devices being positioned to have an overlap zone for their respectively accessible spaces or maneuvering zones in a region of which the measuring supports can be transferred from one handling and transfer device to the other handling and transfer device.

7. An apparatus according to claim 1, wherein the third module comprises plural workstations, each of said workstations adapted for measurement and centrifugation, each of said workstations comprising a disc-shaped supporting base carried by an upper end of a rotating vertical shaft engagable with interlocking or frictional holding in a concentric sleeve of an associated measuring support and a substantially discoidal upper pressing device set into rotation round an axis of symmetry by friction on said associated measuring support, said pressing device comprising one or more annular pressing members and being displaceable reversibly from a high position in which said pressing members are not in contact with the measuring support arranged on the supporting base to plural lower positions in which the pressing members are successively brought to rest on a snugly fitting floating membrane in a predetermined order, said membrane resting in the region of concentric circular or annular sealed contact zones or zones arranged in concentric circular or annular configurations with an upper wall of said associated measuring support.

8. An apparatus for determining the identity and antibiogram of bacteria, said apparatus comprising:

primary receivers;

a first module for receiving and storing measuring supports;

a second module for incubation of said measuring supports;

a third module for nephelometric, photometric, or fluorimetric measurement;

at least one transfer device arranged to serve said first, second, and third modules;

a computer for monitoring, acquiring, registering, processing, evaluating or storing data, said first module comprising at least one means for receiving and storing said primary receivers and a device for calibration of an inoculum in said primary receivers and for preparation of said measuring supports; and a disc-shaped measuring support comprising a rigid main body limiting, in the form of non-communicating enclosures, a cylindrical central chamber and plural associated peripheral compartments each having a catching niche, wherein said main body has an upper wall provided with plural sets of traversing transfer orifices respectively opening into the cylindrical central chamber, into each catching niche allocated to each compartment and into each of said compartments and, with the exception of a central portion surrounding a charging orifice of said central chamber and of a zone of measurement windows of the compartments, covered by a fitted sealed floating membrane fixed locally and hermetically at its external periphery and around the charging orifice and being pressable against an upper face of said upper wall to form sealed temporary zones of contact extending between or covering some of said sets of traversing orifices during rotation of said measuring support.

9. An apparatus according to claim 8, wherein said measuring support upper wall further comprises:

concentric annular grooves or indentations in a region of an upper face of the upper wall, the traversing orifices opening in said annular grooves or indentations and being arranged in spaced concentric circles, an internal groove comprising an internal rib forming an annular contact surface and separating outlet orifices of the central chamber and inlet orifices of an annular concentric chamber comprising radial catching niches, and outlet orifices of the catching niches opening in a region of an upper face of a concentric circular rib or in protruding dome structures arranged in an external groove, the upper ends of the internal rib and the dome structures being located in at least one plane extending back from a plane of adhesion of the snugly fitting sealed membrane.

10. An apparatus of claim 8, wherein said measuring support further comprises a pre-incubation compartment identical to said peripheral compartments, and aligned circularly therewith and communicating with a closed pre-chamber formed in a concentric chamber enclosing catching and equi-distribution niches and adapted for being supplied with inoculum, via a passage not blockable by the sealed temporary zones of contact capable of being formed between the fitted membrane and the upper wall, from an internal catching niche located in a region of a portion of a peripheral lateral wall of the central chamber.

11. An apparatus of claim 10, wherein said measuring support further comprises a pre-chamber supply passage communicating freely with a pre-incubation compartment and also forming an overflow for the catching niches, said supply passage comprising a conduit beginning in an upper part of the portion of the peripheral lateral wall limiting the internal catching niche formed by cooperation between a groove made in an upper part of a radial projecting extension of the peripheral lateral wall of the central chamber and of the upper wall, and opening into or at the inlet of a groove with a centripetal radial extension dug in the upper face of the upper wall, forming a sealed conduit in cooperation with the membrane stuck on either side of said groove and of which a distal end terminates in the region of a traversing orifice opening in the pre-chamber.

12. An apparatus according to claim 8, wherein the charging orifice of the central chamber is located in an indentation in the upper wall and is blockable by a stopper having an upper part, said upper part being substantially level with the upper face of the upper wall, the bottom of the central chamber being surrounded by a concentric gripping and rigidifying sleeve projecting in the region of the lower face of the support, and a traversing aperture having dimensions identical to those of said peripheral compartments and located in circular alignment with said peripheral compartments, is located in the main body and in the upper wall adjacent to a pre-incubation compartment.

13. An apparatus according to claim 8, wherein the upper wall is equipped with first measuring windows, said first measuring windows being above each of said peripheral compartments and close to its external edge, additional measuring windows being provided in each of the wall portions of the main body respectively constituting the bottoms of said compartments opposite each said first measuring window, and at least one indexing reflecting zone formed on an external face of an external peripheral wall of the main body being associated with each of said peripheral compartments with an angular offset which is fixed relative thereto.

14. An apparatus according to claim 8, wherein said primary receiver comprises:

a cylindrical receiver equipped on its bottom with at least one vent tube, an overflow evacuation conduit, a sampling means adapted for sampling a predetermined quantity of inoculum mounted separably by tearing or fitting in the bottom of said primary receiver and eccentric relative to an axis of said primary receiver, and a trough-shaped transverse recess extending between walls of said primary receiver, each end of said recess terminating with a measuring window, said recess also being equipped with a raised part communicating with said recess, said vent, and said overflow conduit, the sampling means being sealed by a tearable film and a closure cover cooperating by sealed conical fitting with a conical upper part of said primary receiver.

15. An apparatus according to claim 14, wherein the conical upper part of said primary receiver comprises at least one shallow notch and two deeper notches of different widths arranged in alignment with one another and at 90° to an axis passing through the shallow notch or notches, said at least one shallow notch being aligned on an axis of the recess of the bottom and the deeper notches cooperating with tabs of a corresponding section provided on the sealed closure cover, said corresponding section being provided on its upper face with a surface extending on the axis of the tabs and with a conical wall having a shape corresponding to the shape of the conical upper part of said primary receiver and connecting the tabs.

16. An apparatus according to claim 8, wherein each of said measuring supports further comprise:

a rotating support with an upper composite disc provided with peripheral compartments adapted for receiving inoculum and antibiotic preparations, said rotating support having a concentric cylindrical body having a smaller diameter than said composite disc and connected to said composite disc, said rotating support forming a central chamber for receiving inoculum for distribution by centrifugation, and said central chamber being supplied through an orifice in an upper face of the upper composite disc and being surrounded by a gripping and rigidifying sleeve.

17. An apparatus according to claim 8, wherein each of said measuring supports further comprise:

a rotating support with an upper composite disc provided with the peripheral compartments for receiving inoculum and a characterizing reagent, said rotating support having a concentric cylindrical body of smaller diameter than the composite disc and being connected to said disc, said concentric cylindrical body forming a concentric sleeve for receiving one of the primary receivers in an inverted position for distribution by centrifugation of the inoculum, said concentric sleeve extending, at the center, beneath a lower face of a circular plate and being connected thereto and being equipped at its free end with a conical wall part, said conical wall part extending internally of said concentric sleeve and being adapted to cooperate with an external wall of the conical upper part of the primary receiver and being surrounded by a gripping and rigidifying concentric sleeve.

18. An apparatus for determining the identity and antibiogram of bacteria, said apparatus comprising:

primary receivers;

a first module for receiving and storing measuring supports;

a second module for incubation of said measuring supports;

a third module for nephelometric, photometric, or fluorimetric measurement;

at least one transfer device arranged to serve said first, second, and third modules;

a computer for monitoring, acquiring, registering, processing, evaluating or storing data, said first module comprising at least one means for receiving and storing said primary receivers and a device for calibration of an inoculum in said primary receivers and for preparation of said measuring supports;

said measuring supports being rotating and comprising an upper composite disc with a circular cover part and a circular plate, said circular cover part having an orifice centrally located, said circular plate having an upper face turned toward a lower face of the cover part, said circular plate carrying compartments extending upwardly on a periphery of said circular plate, the compartments being adapted for receiving inoculum and antibiotic preparations, said circular plate being connected to a central chamber closed by a bottom, said circular cover part being provided with a rim extending concentrically above a circular wall of the circular plate, said rim limiting said compartments extending upwardly toward the exterior and being fixed to said circular wall by adhesion or welding.

19. Apparatus according to claim 18, wherein the circular plate further comprises at least one pre-incubation compartment located between the compartments extending upwardly and connected by a capillary tube to a concentric chamber located beneath the circular plate of the cover part in the central chamber of the circular plate.

20. An apparatus according to claim 19, wherein said upper composite disc further comprises a pit, said pit comprising said orifice and extending concentrically within the concentric chamber, said pit comprising a moving dish adapted to be provided with a dry culture medium, and a basin limited by a sealed guide wall; and a sealing film covering the pit, the upper part of the circular cover plate, and the capillary tube.

21. An apparatus according to claim 18, said composite disc further comprising:

a sensing means for sensing the inoculum during centrifugation, said sensing means being provided with supports, as viewed in the radial direction, in front of each of said compartments, said supports being each connected to an interior of a corresponding compartment by a capillary tube and being open into an internal space communicating with the central chamber of the circular plate forming the lower body part, the compartments each being connected to a circular capillary tube opening by a radial capillary tube, and, via a further capillary tube, to an exterior of the circular cover plate or of the circular cover part, at least one of said compartments being a pre-incubation compartment and being connected directly, by a corresponding passage hole, to the circular capillary tube, said capillary tubes being limited in the upper part of the circular cover part by a sealed film, the capillaries communicating at their end closest to a central axis of the composite disc with the internal chambers by holes pierced in the circular cover part.

22. An apparatus according to claim 18, wherein the circular cover part further comprises:

first measuring windows above each compartment and close to its edge, second measuring windows being provided beneath the lower face of the circular plate or of the composite disc opposite each first measuring window, and at least one indexing reflective zone formed on the external face of the external peripheral wall of the supports and being associated with each compartment with an angular offset which is fixed relative thereto.

23. Apparatus according to claim 22, wherein, for the automatic introduction of an initial bacterial inoculum into a measuring support for antibiogram or simultaneous combined analysis, the primary receiver further comprises:

the form of a container provided with a pipette, the pipette being adapted for transferring the entire content of the primary receiver, said pipette being adapted to be detachable from the primary receiver when used to empty a contents of said pipette into an associated measuring support and replaceable in the primary receiver, said pipette also being detachable and useable to block the associated measuring support by being deposited in a pit of the associated measuring support.

24. An apparatus for determining the identity and antibiogram of bacteria, said apparatus comprising:

primary receivers;

a first module for receiving and storing measuring supports;

a second module for incubation of said measuring supports;

a third module for nephelometric, photometric, or fluorimetric measurement;

at least one transfer device arranged to serve said first, second, and third modules;

a computer for monitoring, acquiring, registering, processing, evaluating or storing data, said first module comprising at least one means for receiving and storing said primary receivers and a device for calibration of an inoculum in said primary receivers and for preparation of said measuring supports; and each of said measuring supports comprising a rotating support with an upper composite disc provided with the peripheral compartments for receiving inoculum and a characterizing reagent, said rotating support having a concentric cylindrical body of smaller diameter than the composite disc and being connected to said disc, said concentric cylindrical body forming a concentric sleeve for receiving one of the primary receivers in an inverted position for distribution by centrifugation of the inoculum, said concentric sleeve extending, at the center, beneath a lower face of a circular plate of said composite disc and being connected thereto and being equipped at its free end with a conical wall part, said conical wall part extending internally of said concentric sleeve and being adapted to cooperate with an external wall of the conical upper part of the primary receiver and being surrounded by a gripping and rigidifying concentric sleeve, said composite disc further comprising a circular cover part, said circular plate being provided with an upper face turned toward a lower face of said circular cover part, and also being providing extending from its periphery with compartments adapted for receiving the inoculum and characterizing reagents, said cover part being provided with a rim extending concentrically above a circular wall of said circular plate limiting said compartments toward the exterior, said rim being fixed to said circular wall by adhesion or welding.

25. An apparatus according to claim 24, said composite disc further comprising:

a sensing means for sensing the inoculum during centrifugation, said sensing means being provided with supports, as viewed in the radial direction, in front of each of said compartments, said supports being each connected to an interior of a corresponding compartment by a capillary tube and being open into an internal space communicating with the central chamber of the circular plate forming the lower body part, the compartments each being connected to a circular capillary tube opening by a radial capillary tube, and, via a further capillary tube, to an exterior of the circular cover plate or of the circular cover part, at least one of said compartments being a pre-incubation compartment and being connected directly, by a corresponding passage hole, to the circular capillary tube, said capillary tubes being limited in the upper part of the circular cover part by a sealed film, the capillaries communicating at their end closest to a central axis of the composite disc with the internal chambers by holes pierced in the circular cover part.

26. An apparatus for bacteria identification and for determination of bacteria sensitivity to antibiotics in antibiogram form, said apparatus comprising:

a primary receiver;

at least one measuring support adapted to be in communication with said primary receiver and adapted to carry out identification, antibiogram or the identification and the antibiogram simultaneously in a single combined operation;

said at least one measuring support comprising plural compartments, at least one of said plural compartments being a reagent-containing compartment;

a sampling tool for manually introducing a given volume of a bacterial colony into said primary receiver;

a transfer means for automatically dispersing the bacterial colony within a liquid to form a precalibrated inoculum in said primary receiver and for automatically at least partially transferring the precalibrated inoculum between said primary receiver and said at least one measuring support, said transfer means being adapted to carry out transfers without the precalibrated inoculum being placed in contact with an element other than the sampling and transfer tool and the primary receiver and a final measuring support, said transfer means being adapted to transfer quantities of the precalibrated inoculum corresponding to quantities required for analysis to be carried out;

a diluting means operatively connected to one of said compartments for diluting the precalibrated inoculum into a diluted inoculum;

said transfer means being adapted to automatically distribute an inoculum sample of the diluted inoculum or the precalibrated inoculum to said reagent-containing compartment for a definitive calibration in said reagent-containing compartment;

a antibiogram multiplication means for carrying out the antibiogram and a pre-growth operation to enable the inoculum sample to multiply before analysis, said antibiogram multiplication means being operatively connected to said transfer means;

a measuring compartment connected to said transfer means and adapted to accept the inoculum sample, said measuring compartment in operative communication with a measurement means for taking measurements, during or at an end of an inoculum incubation period, of the inoculum sample; and a computer, connected to said measurement means, for registering the measurements and for processing the measurements to characterize the growth of bacteria present in the inoculum sample to identify the bacteria or to determine a bacteria sensitivity to antibiotics.

* * * * *